(12) United States Patent
Mei et al.

(10) Patent No.: US 12,410,250 B2
(45) Date of Patent: Sep. 9, 2025

(54) ANTI-CD47 ANTIBODIES AND USES THEREOF

(71) Applicant: WUXI BIOLOGICS IRELAND LIMITED, Dundalk (IE)

(72) Inventors: Qin Mei, Shanghai (CN); Fagen Hu, Shanghai (CN); Jing Li, Shanghai (CN); Jiaxiang Shao, Shanghai (CN); Yuhong Shen, Shanghai (CN)

(73) Assignee: WUXI BIOLOGICS IRELAND LIMITED, Dundalk (IE)

( * ) Notice: Subject to any disclaimer, the term of this patent is extended or adjusted under 35 U.S.C. 154(b) by 644 days.

(21) Appl. No.: 17/770,039

(22) PCT Filed: Oct. 23, 2020

(86) PCT No.: PCT/CN2020/123027
§ 371 (c)(1),
(2) Date: Apr. 18, 2022

(87) PCT Pub. No.: WO2021/078219
PCT Pub. Date: Apr. 29, 2021

(65) Prior Publication Data
US 2022/0403023 A1 Dec. 22, 2022

(30) Foreign Application Priority Data
Oct. 25, 2019 (WO) ................ PCT/CN2019/113296

(51) Int. Cl.
*C07K 16/28* (2006.01)
*A61K 39/00* (2006.01)
*A61K 39/395* (2006.01)
*A61K 45/06* (2006.01)
*A61P 35/00* (2006.01)

(52) U.S. Cl.
CPC .... *C07K 16/2803* (2013.01); *A61K 39/39558* (2013.01); *A61K 45/06* (2013.01); *A61P 35/00* (2018.01); *A61K 2039/505* (2013.01); *C07K 2317/52* (2013.01); *C07K 2317/565* (2013.01); *C07K 2317/732* (2013.01); *C07K 2317/734* (2013.01); *C07K 2317/92* (2013.01)

(58) Field of Classification Search
None
See application file for complete search history.

(56) References Cited

U.S. PATENT DOCUMENTS

| 10,239,945 B2 | 3/2019 | Manning et al. |
| 2017/0081407 A1 | 3/2017 | Grosveld et al. |
| 2019/0270817 A1 | 9/2019 | Ali et al. |
| 2020/0181259 A1 | 6/2020 | Tsun et al. |
| 2020/0377593 A1 | 12/2020 | Liu et al. |

FOREIGN PATENT DOCUMENTS

| JP | 2018535692 A | 12/2018 |
| WO | WO 2013/119714 A1 | 8/2013 |
| WO | WO 2014/087248 A2 | 6/2014 |
| WO | WO 2015/191861 A1 | 12/2015 |
| WO | WO 2016/081423 A1 | 5/2016 |
| WO | WO 2016/109415 A1 | 7/2016 |
| WO | WO 2017/053423 A1 | 3/2017 |
| WO | WO 2017/121771 A1 | 7/2017 |
| WO | WO 2018/075857 A1 | 4/2018 |
| WO | WO 2018/137705 A1 | 8/2018 |
| WO | WO 2018/142322 A1 | 8/2018 |
| WO | WO 2019/042119 A1 | 3/2019 |
| WO | WO 2019/042285 A1 | 3/2019 |
| WO | WO 2019/179366 A1 | 9/2019 |
| WO | WO 2019/184912 A1 | 10/2019 |
| WO | WO 2021/213511 A1 | 10/2021 |

OTHER PUBLICATIONS

Liu et al., "Pre-Clinical Development of a Humanized Anti-CD47 Antibody with Anti-Cancer Therapeutic Potential", PLOS ONE, Sep. 2015, 10(9): e0137345, 23 pages.

*Primary Examiner* — Janet L Epps-Smith
*Assistant Examiner* — Sarah A Alsomairy
(74) *Attorney, Agent, or Firm* — James S. Keddie; Bozicevic, Field & Francis LLP

(57) ABSTRACT

Provided are anti-CD47 antibodies, the nucleic acid molecules encoding the anti-CD47 antibodies, expression vectors and host cells used for the expression of anti-CD47 antibodies. Provided are methods for validating the function of antibodies. The antibodies provide a potent agent for the treatment of cancers via modulating immune functions.

20 Claims, 12 Drawing Sheets
Specification includes a Sequence Listing.

A

B

C

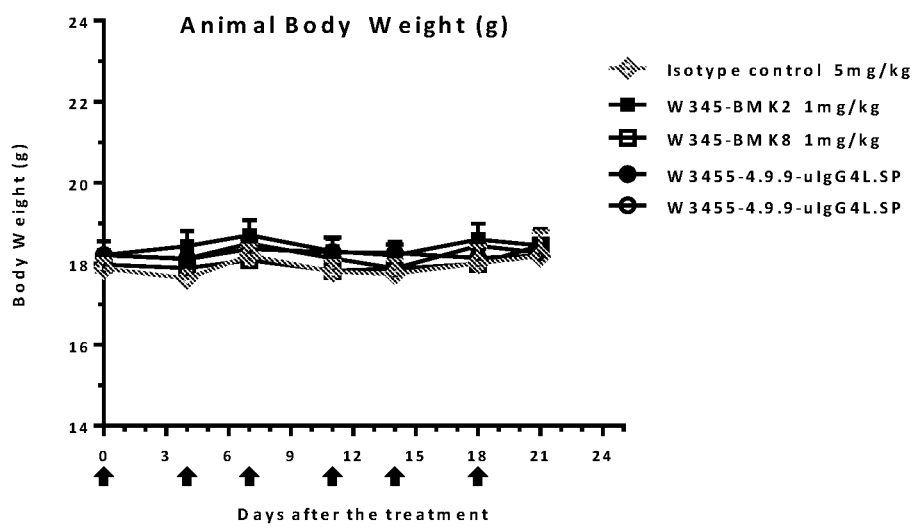
Figure 19A
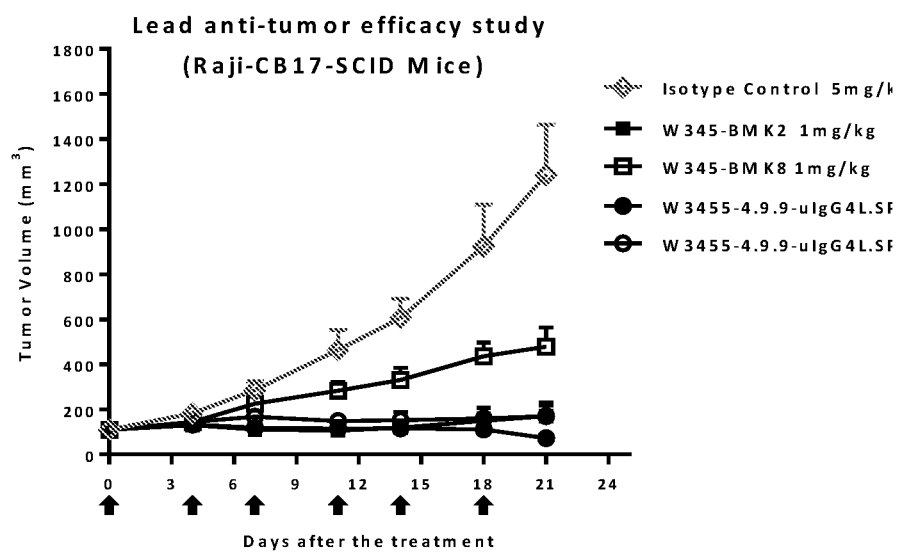

SEQUENCE LISTING

```
<160> NUMBER OF SEQ ID NOS: 12

<210> SEQ ID NO 1
<211> LENGTH: 10
<212> TYPE: PRT
<213> ORGANISM: Artificial sequence
<220> FEATURE:
<223> OTHER INFORMATION: Synthesized sequence

<400> SEQUENCE: 1

Gly Phe Thr Phe Ser Asn Phe Ala Met Ser
1               5                   10

<210> SEQ ID NO 2
<211> LENGTH: 17
<212> TYPE: PRT
<213> ORGANISM: Artificial sequence
<220> FEATURE:
<223> OTHER INFORMATION: Synthesized sequence

<400> SEQUENCE: 2

Thr Ile Ser Ala Ser Gly Gly Arg Thr Phe Tyr Ala Asp Ser Val Lys
1               5                   10                  15

Gly

<210> SEQ ID NO 3
<211> LENGTH: 10
<212> TYPE: PRT
<213> ORGANISM: Artificial sequence
<220> FEATURE:
<223> OTHER INFORMATION: Synthesized sequence

<400> SEQUENCE: 3

Glu Gly Ser Phe Gly Glu Gly Val Asp Pro
1               5                   10

<210> SEQ ID NO 4
<211> LENGTH: 11
<212> TYPE: PRT
<213> ORGANISM: Artificial sequence
<220> FEATURE:
<223> OTHER INFORMATION: Synthesized sequence

<400> SEQUENCE: 4

Ser Gly Asp Ala Leu Pro Lys Lys Tyr Ala Tyr
1               5                   10

<210> SEQ ID NO 5
<211> LENGTH: 7
<212> TYPE: PRT
<213> ORGANISM: Artificial sequence
<220> FEATURE:
<223> OTHER INFORMATION: Synthesized sequence

<400> SEQUENCE: 5

Glu Asp Asn Lys Arg Pro Ser
1               5

<210> SEQ ID NO 6
<211> LENGTH: 11
<212> TYPE: PRT
<213> ORGANISM: Artificial sequence
<220> FEATURE:
<223> OTHER INFORMATION: Synthesized sequence

<400> SEQUENCE: 6
```

Tyr Ser Thr Asp Ile Ser Gly Asn His Trp Val
1               5                   10

<210> SEQ ID NO 7
<211> LENGTH: 119
<212> TYPE: PRT
<213> ORGANISM: Artificial sequence
<220> FEATURE:
<223> OTHER INFORMATION: Synthesized sequence

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Ala Met Ser Trp Val Arg Gln Ala Pro Gly Lys Gly Leu Glu Trp Val
        35                  40                  45

Ser Thr Ile Ser Ala Ser Gly Gly Arg Thr Phe Tyr Ala Asp Ser Val
    50                  55                  60

Lys Gly Arg Ile Thr Ile Ser Arg Asp Asn Ser Lys Asn Thr Leu Phe
65                  70                  75                  80

Leu Gln Met Asn Gly Leu Arg Ala Glu Asp Thr Ala Val Tyr Tyr Cys
                85                  90                  95

Ala Lys Glu Gly Ser Phe Gly Glu Gly Val Asp Pro Trp Gly Gln Gly
            100                 105                 110

Thr Leu Val Thr Val Ser Ser
        115

<210> SEQ ID NO 8
<211> LENGTH: 108
<212> TYPE: PRT
<213> ORGANISM: Artificial sequence
<220> FEATURE:
<223> OTHER INFORMATION: Synthesized sequence

<400> SEQUENCE: 8

Ser Tyr Glu Met Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Asp Asn Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ile Ser Gly Asn His
                85                  90                  95

Trp Val Phe Gly Gly Gly Thr Glu Leu Thr Val Leu
            100                 105

<210> SEQ ID NO 9
<211> LENGTH: 357
<212> TYPE: DNA
<213> ORGANISM: Artificial sequence
<220> FEATURE:
<223> OTHER INFORMATION: Synthesized sequence

<400> SEQUENCE: 9
gaagtgcagt tgttggagtc tgggggaggc ttggtacagc ctggggggtc cctgagactc      60

```
tcctgtgcag cctctggatt cacctttagc aactttgcca tgagctgggt ccgccaggct    120
ccagggaagg ggctggagtg ggtctcaact attagtgcta gtggtggtcg acattctac    180 gcagactccg tgaagggccg gatcaccatc tccagagaca attccaagaa cacgctgttt    240
ctgcaaatga atggcctgag agccgaggac acggccgtct attactgtgc gaaggagggg    300
tcgttcgggg agggagtcga ccctggggc cagggaaccc tggtcaccgt gtcctca       357
```

<210> SEQ ID NO 10
<211> LENGTH: 324
<212> TYPE: DNA
<213> ORGANISM: Artificial sequence
<220> FEATURE:
<223> OTHER INFORMATION: Synthesized sequence

<400> SEQUENCE: 10

```
tcctatgaga tgacacagcc accctcggtg tcagtgtccc caggacaaac ggccaggatc     60
acctgctctg gagatgcatt gccaaaaaaa tatgcttatt ggtaccagca gaagtcaggc    120
caggcccctg tgctggtcat ctatgaggac aacaaacgac cctcagggat ccctgagaga    180
ttctctggct ccagctcagg gacaatggcc accttgacta tcagtggggc ccaggtggag    240
gatgaagctg actactactg ttactcaaca gacatcagtg gtaatcattg ggtgttcggc    300
ggagggaccg agctgaccgt ccta                                           324
```

<210> SEQ ID NO 11
<211> LENGTH: 446
<212> TYPE: PRT
<213> ORGANISM: Artificial sequence
<220> FEATURE:
<223> OTHER INFORMATION: Synthesized sequence

<400> SEQUENCE: 11

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Ala Met Ser Trp Val Arg Gln Ala Pro Gly Lys Gly Leu Glu Trp Val
        35                  40                  45

Ser Thr Ile Ser Ala Ser Gly Gly Arg Thr Phe Tyr Ala Asp Ser Val
    50                  55                  60

Lys Gly Arg Ile Thr Ile Ser Arg Asp Asn Ser Lys Asn Thr Leu Phe
65                  70                  75                  80

Leu Gln Met Asn Gly Leu Arg Ala Glu Asp Thr Ala Val Tyr Tyr Cys
                85                  90                  95

Ala Lys Glu Gly Ser Phe Gly Glu Gly Val Asp Pro Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

-continued

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
        210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 12
<211> LENGTH: 214
<212> TYPE: PRT
<213> ORGANISM: Artificial sequence
<220> FEATURE:
<223> OTHER INFORMATION: Synthesized sequence

<400> SEQUENCE: 12

Ser Tyr Glu Met Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Asp Asn Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ile Ser Gly Asn His
                85                  90                  95

Trp Val Phe Gly Gly Gly Thr Glu Leu Thr Val Leu Gly Gln Pro Lys
            100                 105                 110

-continued

```
Ala Ala Pro Ser Val Thr Leu Phe Pro Pro Ser Ser Glu Glu Leu Gln
        115                 120             125

Ala Asn Lys Ala Thr Leu Val Cys Leu Ile Ser Asp Phe Tyr Pro Gly
    130                 135             140

Ala Val Thr Val Ala Trp Lys Ala Asp Ser Ser Pro Val Lys Ala Gly
145                 150             155                 160

Val Glu Thr Thr Thr Pro Ser Lys Gln Ser Asn Asn Lys Tyr Ala Ala
                165             170             175

Ser Ser Tyr Leu Ser Leu Thr Pro Glu Gln Trp Lys Ser His Arg Ser
            180             185             190

Tyr Ser Cys Gln Val Thr His Glu Gly Ser Thr Val Glu Lys Thr Val
        195             200             205

Ala Pro Thr Glu Cys Ser
    210
```

ANTI-CD47 ANTIBODIES AND USES THEREOF

CROSS-REFERENCE TO RELATED APPLICATION

The application is a § 371 national phase of International Application No. PCT/CN2020/123027, filed on Oct. 23, 2020, which claims priority to International application PCT/CN2019/113296, filed Oct. 25, 2019, the entire contents of both applications are hereby incorporated by reference.

SEQUENCE LISTING

The present application is filed with a Sequence Listing in electronic form. The entire contents of the Sequence Listing are hereby incorporated by reference.

FIELD

This application generally relates to antibodies. More specifically, the application relates to monoclonal antibodies against CD47, a method for preparing the same, and the use of the antibodies.

BACKGROUND

Cluster of differentiation 47 (CD47), also known as integrin-associated protein (IAP), is a ~50 kDa immunoglobulin superfamily membrane protein that is a ubiquitous cell surface glycoprotein expressed on most normal cell types. CD47 interacts with its ligand, signal regulatory protein alpha (SIRPα) expressed on macrophages, and then sending an anti-phagocytic or "don't eat me" signal to macrophages and therefore evading immune surveillance [1]. Analysis of various malignant tumors reveals that CD47 is overexpressed on AML, NHL, breast cancer, NSCC and ovarian cells, and the increased CD47 expression correlated with a worse clinical prognosis. These data indicated CD47 may serve as a new immune checkpoint for cancer therapy by blocking CD47-SIRPa interaction and switching-off "don't eat me" signal.

CD47 is a widely expressed cell surface protein that functions as a mediator of phagocytosis through cells of the innate and adaptive immune systems, such as macrophages and dendritic cells. CD47 is overly expressed on many kinds of tumors, including hematological malignancies and solid tumors. More and more research findings have shown targeting CD47-SIRPα signal axis could serve as a new immune checkpoint in cancer immunotherapy, and may have potent anti-tumors ability either with single or combination therapy, making CD47 a universal target in multiple human malignant cancers.

Several anti-CD47 monoclonal antibodies (mAbs) have achieved effective macrophage involved phagocytosis against AML, NHL, breast cells, and ovarian cells. Besides, anti-CD47 mAb combined with approved antibodies (anti-tumor-associated antigen) or using dual-targeting bispecific antibodies have efficiently enhanced anti-tumor activity [2-4]. Based on these preclinical studies, more than six anti-CD47 mAbs and three SIRPα fusion proteins are in active phase I or II clinical trials, covering human hematological malignancies and solid tumors.

However, there is still an ongoing need to develop novel anti-CD47 molecules that are capable of blocking CD47-SIRPα interaction and inducing potent phagocytosis of tumor cells, for use in the prevention or treatment of various diseases including cancers.

SUMMARY

These and other objectives are provided for by the present disclosure which, in a broad sense, is directed to compounds, methods, compositions and articles of manufacture that provide antibodies with improved efficacy. The benefits provided by the present disclosure are broadly applicable in the field of antibody therapeutics and diagnostics and may be used in conjunction with antibodies that react with a variety of targets.

In the present disclosure, a fully human anti-CD47 monoclonal antibody has been generated. The antibodies of the present disclosure can bind to human CD47 or cynomolgus monkey CD47 with a high affinity; effectively block the interaction between CD47 and its ligand SIRPα; show weak binding to human red blood cells (RBCs) and do not induce hemagglutination of human RBCs; induce potent macrophage-mediated phagocytosis of tumor cells with reduced phagocytosis of red blood cells; and exhibit potent tumor growth inhibition.

In some aspects, the present disclosure provides an isolated antibody or an antigen-binding portion thereof against CD47.

In some embodiments, the isolated antibody or the antigen-binding portion thereof as described herein comprises:
A) one or more heavy chain CDRs (HCDRs) selected from the group consisting of:
  (i) a HCDR1 with at least 90% sequence identity to a HCDR1 as set forth in SEQ ID NO: 1;
  (ii) a HCDR2 with at least 90% sequence identity to a HCDR2 as set forth in SEQ ID NO: 2; and
  (iii) a HCDR3 with at least 90% sequence identity to a HCDR3 as set forth in SEQ ID NO: 3;
B) one or more light chain CDRs (LCDRs) selected from the group consisting of:
  (i) a LCDR1 with at least 90% sequence identity to a LCDR1 as set forth in SEQ ID NO: 4;
  (ii) a LCDR2 with at least 90% sequence identity to a LCDR2 as set forth in SEQ ID NO: 5; and
  (iii) a LCDR3 with at least 90% sequence identity to a LCDR3 as set forth in SEQ ID NO: 6; or
C) one or more HCDRs of A) and one or more LCDRs of B).

In some embodiments, the isolated antibody or the antigen-binding portion thereof as described herein comprises:
A) one or more heavy chain CDRs (HCDRs) selected from the group consisting of:
  (i) a HCDR1 comprising SEQ ID NO: 1 or a HCDR1 that differs in amino acid sequence from the HCDR1 by an amino acid addition, deletion or substitution of not more than 2 amino acids;
  (ii) a HCDR2 comprising SEQ ID NO: 2 or a HCDR2 that differs in amino acid sequence from the HCDR2 by an amino acid addition, deletion or substitution of not more than 2 amino acids; and
  (iii) a HCDR3 comprising SEQ ID NO: 3 or a HCDR3 that differs in amino acid sequence from the HCDR3 by an amino acid addition, deletion or substitution of not more than 2 amino acids;
B) one or more light chain CDRs (LCDRs) selected from the group consisting of:
  (i) a LCDR1 comprising SEQ ID NO: 4 or a LCDR1 that differs in amino acid sequence from the LCDR1 by an amino acid addition, deletion or substitution of not more than 2 amino acids;
(ii) a LCDR2 comprising SEQ ID NO: 5 or a LCDR2 that differs in amino acid sequence from the LCDR2 by an amino acid addition, deletion or substitution of not more than 2 amino acids; and
(iii) a LCDR3 comprising SEQ ID NO: 6 or a LCDR3 that differs in amino acid sequence from the LCDR3 by an amino acid addition, deletion or substitution of not more than 2 amino acids; or
C) one or more HCDRs of A) and one or more LCDRs of B).

In some embodiments, the isolated antibody or the antigen-binding portion thereof as described herein comprises a heavy chain variable region (VH) and a light chain variable region (VL), wherein
(A) the VH comprises:
 (i) a HCDR1 comprising SEQ ID NO: 1;
 (ii) a HCDR2 comprising SEQ ID NO: 2; and
 (iii) a HCDR3 comprising SEQ ID NO: 3; and/or
(B) the VL comprises:
 (i) a LCDR1 comprising SEQ ID NO: 4;
 (ii) a LCDR2 comprising SEQ ID NO: 5; and
 (iii) a LCDR3 comprising SEQ ID NO: 6.

In some embodiments, the isolated antibody or the antigen-binding portion thereof as described herein comprises:
(A) a heavy chain variable region comprising:
 (i) the amino acid sequence of SEQ ID NO:7;
 (ii) an amino acid sequence at least 85%, 90%, or 95% identical to SEQ ID NO:7; or
 (iii) an amino acid sequence with addition, deletion and/or substitution of one or more amino acids compared with SEQ ID NO: 7; and/or
(B) a light chain variable region comprising:
 (i) the amino acid sequence of SEQ ID NO: 8;
 (ii) an amino acid sequence at least 85%, at least 90%, or at least 95% identical to SEQ ID NO: 8; or
 (iii) an amino acid sequence with addition, deletion and/or substitution of one or more amino acids compared with SEQ ID NO: 8.

In some embodiments, the isolated antibody or the antigen-binding portion thereof as described herein comprises a heavy chain variable region as set forth in SEQ ID NO: 7 and a light chain variable region as set forth in SEQ ID NO: 8.

In some embodiments, the isolated antibody or the antigen-binding portion thereof further comprises a Fc region of a human IgG, such as IgG4. In some embodiments, the Fc region of human IgG4 comprises a substitution of S228P, according to EU numbering.

In some embodiments, the isolated antibody or the antigen-binding portion thereof as disclosed herein have one or more of the following properties:
(a) specifically binding to human CD47 and cynomolgus monkey CD47, expressed either as soluble proteins or on cell surfaces;
(b) effectively blocking the binding of CD47 to SIRPα, e.g. with an inhibitory rate >85%;
(c) weak binding to red blood cells (RBCs) and avoiding inducing hemagglutination of human RBCs;
(d) inducing potent macrophage-mediated phagocytosis of tumor cells with reduced phagocytosis of human RBCs;
(e) inducing weak or no ADCC and CDC activity on tumor cells;
(f) having good thermal stability and being stable in human serum;
(g) significantly inducing tumor growth inhibition in vivo in animal tumor models; and
(h) exhibiting a synergic effect when administered in combination with other anti-tumor molecules, especially panitumumab.

In certain embodiments, the isolated antibody or the antigen-binding portion thereof as disclosed herein effectively block the binding of CD47 to SIRPα. For example, at least 70%, at least 75%, at least 80%, or at least 85% of the binding between CD47 and SIRPα can be blocked by the antibody or the antigen-binding portion herein. Meanwhile, the antibody or the antigen-binding portion herein could cause significantly less hemagglutination of human RBCs than a benchmark anti-CD47 antibody, for example, cause less than 90%, 80%, 70%, 60%, 50%, 40%, 30%, 20%, 10% or less hemagglutination of human RBCs compared to a benchmark anti-CD47 antibody. Exemplary benchmark antibodies include BMK1, BMK2, BMK4 and BMK8 antibodies, as shown in Table 2.

In some aspects, the present disclosure is directed to an isolated nucleic acid molecule, comprising a nucleic acid sequence encoding the heavy chain variable region and/or the light chain variable region of the isolated antibody as disclosed herein.

In some aspects, the present disclosure is directed to a vector comprising the nucleic acid molecule encoding the antibody or antigen-binding portion thereof as disclosed herein.

In some aspects, the present disclosure is directed to a host cell comprising the expression vector as disclosed herein.

In some aspects, the present disclosure is directed to a pharmaceutical composition comprising at least one antibody or antigen-binding portion thereof as disclosed herein and a pharmaceutically acceptable carrier.

In some aspects, the present disclosure is directed to a method for preparing an anti-CD47 antibody or antigen-binding portion thereof which comprises expressing the antibody or antigen-binding portion thereof in the host cell as disclosed herein and isolating the antibody or antigen-binding portion thereof from the host cell.

In some aspects, the present disclosure is directed to a method of modulating an immune response in a subject, comprising administering the antibody or antigen-binding portion thereof as disclosed herein to the subject such that an immune response in the subject is modulated, optionally the immune response is CD47 related.

In some aspects, the present disclosure is directed to a method for inhibiting growth of tumor cells in a subject, comprising administering an effective amount of the antibody or antigen-binding portion thereof or the pharmaceutical composition as disclosed herein to the subject.

In some aspects, the present disclosure is directed to a method for treating or preventing diseases comprising proliferative disorders (such as cancers) in a subject comprising administering an effective amount of the antibody or antigen-binding portion thereof or the pharmaceutical composition as disclosed herein to the subject.

In some embodiments, the antibody or antigen-binding portion thereof as disclosed herein may be administered (e.g. sequentially or simultaneously) with a chemotherapeutic agent or therapeutic antibody, such as panitumumab.

In some aspects, the present disclosure is directed to the use of the antibody or antigen-binding portion thereof as disclosed herein in the manufacture of a medicament for treating or preventing diseases comprising proliferative disorders (such as cancers).

In some embodiments, said cancer can be a hematological cancer or a solid tumor. The hematological cancer can be selected from e.g. acute lymphoblastic leukemia (ALL), T-ALL, B-ALL, acute myelogenous leukemia (AML), Non-Hodgkin lymphoma, B-lymphoblastic leukemia/lymphoma; B-cell chronic lymphocytic leukemia, chronic lymphocytic leukemia (CLL), chronic myelocytic leukemia (CIVIL), Burkitt's lymphoma, follicular lymphoma, SLL, CNS lymphoma, Richter's Syndrome, multiple myeloma, and immunoblastic large cell lymphoma. In some embodiments, the cancer to be treated is a Burkitt's lymphoma. The solid tumor can be selected from e.g. lung cancer, pancreas cancer, breast cancer, liver cancer, ovary cancer, testicle cancer, kidney cancer, bladder cancer, brain cancer, cervix cancer, colon/rectum cancer, gastrointestinal tract cancer, skin cancer, prostate cancer. In some embodiments, the cancer to be treated is a colon cancer.

In some aspects, the present disclosure is directed to kits or devices and associated methods that employ the antibody or antigen-binding portion thereof as disclosed herein, and pharmaceutical compositions as disclosed herein, which are useful for the treatment of diseases comprising cancers.

The foregoing is a summary and thus contains, by necessity, simplifications, generalizations, and omissions of detail; consequently, those skilled in the art will appreciate that the summary is illustrative only and is not intended to be in any way limiting. Other aspects, features, and advantages of the methods, compositions and/or devices and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE FIGURES

FIGS. 19A-19B shows the body weight changes (A) and tumor volume changes (B) in CB-17 SCID mice inoculated with Raji cells after administration of lead antibody W3455, BMK2 or BM K8.

DETAILED DESCRIPTION

Figure 1:
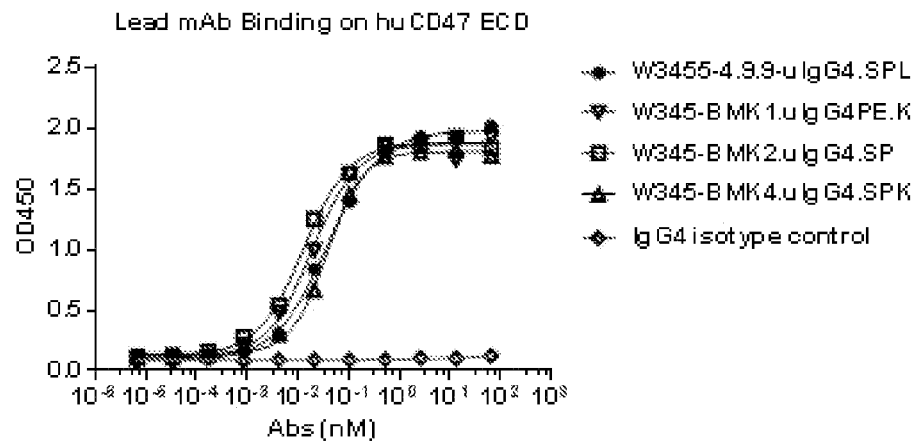
FIG. 1 shows the binding of lead antibody W3455-4.9.9-uIgG4.SPL (abbreviated as "W3455" herein) to human CD47, as measured by ELISA. W345-BMK1.uIgG4PE.K, W345-BMK2.uIgG4. SP and W345-BMK4.uIgG4.SPK are anti-CD47 benchmark antibodies. IgG4 isotype is an isotype control. The "Neg" column is the max OD of a blank control.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

Unless otherwise defined herein, scientific and technical terms used in the specification have the meanings that are commonly understood by those of ordinary skill in the art. Further, unless otherwise required by context, singular terms shall include pluralities and plural terms shall include the singular. More specifically, as used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like. In this application, the use of "or" means "and/or" unless stated otherwise. Furthermore, the use of the term "comprising," as well as other forms, such as "comprises" and "comprised," is not limiting. In addition, ranges provided in the specification and appended claims include both end points and all points between the end points.

Generally, nomenclature used in connection with, and techniques of, cell and tissue culture, molecular biology, immunology, microbiology, genetics and protein and nucleic acid chemistry and hybridization described herein are those well-known and commonly used in the art. The methods and techniques of the present disclosure are generally performed according to conventional methods well known in the art and as described in various general and more specific references that are cited and discussed throughout the present specification unless otherwise indicated. See, e.g., Abbas et al., Cellular and Molecular Immunology, 6$^{th}$ ed., W. B. Saunders Company (2010); Sambrook J. & Russell D. *Molecular Cloning: A Laboratory Manual,* 3rd ed., Cold Spring Harbor Laboratory Press, Cold Spring Harbor, N.Y. (2000); Ausubel et al., *Short Protocols in Molecular Biology: A Compendium of Methods from Current Protocols in Molecular Biology,* Wiley, John & Sons, Inc. (2002); Harlow and Lane *Using Antibodies: A Laboratory Manual*, Cold Spring Harbor Laboratory Press, Cold Spring Harbor, N.Y. (1998); and Coligan et al., *Short Protocols in Protein Science*, Wiley, John & Sons, Inc. (2003). The nomenclature used in connection with, and the laboratory procedures and techniques of, analytical chemistry, synthetic organic chemistry, and medicinal and pharmaceutical chemistry described herein are those well-known and commonly used in the art. Moreover, any section headings used herein are for organizational purposes only and are not to be construed as limiting the subject matter described.

Definitions

Definitions and explanations of relevant terms or expressions are provided as follows.

The term "antibody" or "Ab," as used herein, generally refers to a Y-shaped tetrameric protein comprising two heavy (H) and two light (L) polypeptide chains held together by covalent disulfide bonds and non-covalent interactions. Light chains of an antibody may be classified into κ and λ light chain. Heavy chains may be classified into μ, δ, γ, α and ε, which define isotypes of an antibody as IgM, IgD, IgG, IgA and IgE, respectively. In a light chain and a heavy chain, a variable region is linked to a constant region via a "J" region of about 12 or more amino acids, and a heavy chain further comprises a "D" region of about 3 or more amino acids. Each heavy chain consists of a heavy chain variable region ($V_H$) and a heavy chain constant region ($C_H$). A heavy chain constant region consists of 3 domains ($C_H1$, $C_H2$ and $C_H3$). Each light chain consists of a light chain variable region ($V_L$) and a light chain constant region ($C_L$). $V_H$ and $V_L$ region can further be divided into hypervariable regions (called complementary determining regions (CDR)), which are interspaced by relatively conservative regions (called framework region (FR)). Each $V_H$ and $V_L$ consists of 3 CDRs and 4 FRs in the following order: FR1, CDR1, FR2, CDR2, FR3, CDR3, FR4 from N-terminal to C-terminal. The variable region ($V_H$ and $V_L$) of each heavy/light chain pair forms antigen binding sites, respectively. Distribution of amino acids in various regions or domains follows the definition in Kabat Sequences of Proteins of Immunological Interest (National Institutes of Health, Bethesda, Md. (1987 and 1991)), or Chothia & Lesk (1987) J. Mol. Biol. 196: 901-917; Chothia et al., (1989) Nature 342:878-883. Antibodies may be of different antibody isotypes, for example, IgG (e.g., IgG1, IgG2, IgG3 or IgG4 subtype), IgA1, IgA2, IgD, IgE or IgM antibody.

The term "antigen-binding portion" or "antigen-binding fragment" of an antibody, which can be interchangeably used in the context of the application, refers to polypeptides comprising fragments of a full-length antibody, which retain the ability of specifically binding to an antigen that the full-length antibody specifically binds to, and/or compete with the full-length antibody for binding to the same antigen. Generally, see Fundamental Immunology, Ch. 7 (Paul, W., ed., the second edition, Raven Press, N.Y. (1989), which is incorporated herein by reference for all purposes. Antigen binding fragments of an antibody may be produced by recombinant DNA techniques or by enzymatic or chemical cleavage of an intact antibody. Under some conditions, antigen binding fragments include Fab, Fab', F(ab')$_2$, Fd, Fv, dAb and complementary determining region (CDR) fragments, single chain antibody (e.g. scFv), chimeric antibody, diabody and such polypeptides that comprise at least part of antibody sufficient to confer the specific antigen binding ability on the polypeptides. Antigen binding fragments of an antibody may be obtained from a given antibody (e.g., the monoclonal anti-human X antibody provided in the instant application) by conventional techniques known by a person skilled in the art (e.g., recombinant DNA technique or enzymatic or chemical cleavage methods), and may be screened for specificity in the same manner by which intact antibodies are screened.

The term "monoclonal antibody" or "mAb," as used herein, refer to a preparation of antibody molecules of single molecular composition. A monoclonal antibody displays a single binding specificity and affinity for a particular epitope.

The term "human antibody" or "fully human antibody," as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies may include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences.

The term "human monoclonal antibody," as used herein, refers to antibodies displaying a single binding specificity, which have variable regions in which both the framework and CDR regions are derived from human germline immunoglobulin sequences.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody," as used herein, refers to an antibody in which the variable region sequences are derived from one species and the constant region sequences are derived from another species, such as an antibody in which the variable region sequences are derived from a mouse antibody and the constant region sequences are derived from a human antibody.

The term "recombinant antibody," as used herein, refers to an antibody that is prepared, expressed, created or isolated by recombinant means, such as antibodies isolated from an animal that is transgenic for another species' immunoglobulin genes, antibodies expressed using a recombinant expression vector transfected into a host cell, antibodies isolated from a recombinant, combinatorial antibody library, or antibodies prepared, expressed, created or isolated by any other means that involves splicing of immunoglobulin gene sequences to other DNA sequences.

The term "Ka," as used herein, is intended to refer to the association rate of a particular antibody-antigen interaction, whereas the term "Kd" as used herein, is intended to refer to the dissociation rate of a particular antibody-antigen interaction. Kd values for antibodies can be determined using methods well established in the art. The term "$K_D$" as used herein, is intended to refer to the dissociation constant of a particular antibody-antigen interaction, which is obtained from the ratio of Kd to Ka (i.e., Kd/Ka) and is expressed as a molar concentration (M). A preferred method for determining the Kd of an antibody is by using surface plasmon resonance, preferably using a biosensor system such as a Biacore® system.

The term "specific binding" or "specifically binds" as used herein refers to a non-random binding reaction between two molecules, such as for example between an antibody and an antigen.

The ability of "inhibit binding" or "block binding", as used herein, refers to the ability of an antibody to inhibit the binding interaction between two molecules (e.g., CD47 and its ligand) to any detectable level. In certain embodiments, the binding of the two molecules can be inhibited at least 50% by the antibody or antigen-binding fragment thereof. In certain embodiments, such an inhibitory effect may be greater than 60%, greater than 70%, greater than 80%, greater than 85%, or greater than 90%.

The term "high affinity" for an IgG antibody, as used herein, refers to an antibody having a $K_D$ of $1\times10^{-7}$ M or less, more preferably $5\times10^{-8}$ M or less, even more preferably $1\times10^{-8}$ M or less, even more preferably $5\times10^{-9}$ M or less, even more preferably $1\times10^{-9}$ M or less, even more preferably $5\times10^{-10}$ M or less, even more preferably $1\times10^{-10}$ M or less, even more preferably $5\times10^{-11}$ M or less, even more preferably $4\times10^{-11}$ M or less, even more preferably $3\times10^{-11}$ M or less, and even more preferably $2.5\times10^{-11}$ M or less for a target antigen, as determined by SPR.

The term "$EC_{50}$," as used herein, which is also termed as "half maximal effective concentration" refers to the concentration of a drug, antibody or toxicant which induces a response halfway between the baseline and maximum after a specified exposure time. In the context of the application, $EC_{50}$ is expressed in the unit of "nM".

The term "epitope," as used herein, refers to a portion on antigen that an immunoglobulin or antibody specifically binds to. "Epitope" is also known as "antigenic determinant". Epitope or antigenic determinant generally consists of chemically active surface groups of a molecule such as amino acids, carbohydrates or sugar side chains, and generally has a specific three-dimensional structure and a specific charge characteristic. For example, an epitope generally comprises at least 3, 4, 5, 6, 7, 8, 9, 10, 11, 12, 13, 14 or 15 consecutive or non-consecutive amino acids in a unique steric conformation, which may be "linear" or "conformational". See, for example, Epitope Mapping Protocols in Methods in Molecular Biology, Vol. 66, G. E. Morris, Ed. (1996). In a linear epitope, all the interaction sites between a protein and an interaction molecule (e.g., an antibody) are present linearly along the primary amino acid sequence of the protein. In a conformational epitope, the interaction sites span over amino acid residues that are separate from each other in a protein. Antibodies may be screened depending on competitiveness of binding to the same epitope by conventional techniques known by a person skilled in the art. For example, study on competition or cross-competition may be conducted to obtain antibodies that compete or cross-compete with each other for binding to antigens (e.g. RSV fusion protein). High-throughput methods for obtaining antibodies binding to the same epitope, which are based on their cross-competition, are described in an international patent application WO 03/48731.

The term "isolated," as used herein, refers to a state obtained from natural state by artificial means. If a certain "isolated" substance or component is present in nature, it is possible because its natural environment changes, or the substance is isolated from natural environment, or both. For example, a certain un-isolated polynucleotide or polypeptide naturally exists in a certain living animal body, and the same polynucleotide or polypeptide with a high purity isolated from such a natural state is called isolated polynucleotide or polypeptide. The term "isolated" excludes neither the mixed artificial or synthesized substance nor other impure substances that do not affect the activity of the isolated substance.

The term "vector," as used herein, refers to a nucleic acid vehicle which can have a polynucleotide inserted therein. When the vector allows for the expression of the protein encoded by the polynucleotide inserted therein, the vector is called an expression vector. The vector can have the carried genetic material elements expressed in a host cell by transformation, transduction, or transfection into the host cell. Vectors are well known by a person skilled in the art, including, but not limited to plasmids, phages, cosmids, artificial chromosome such as yeast artificial chromosome (YAC), bacterial artificial chromosome (BAC) or P1-derived artificial chromosome (PAC); phage such as λ phage or M13 phage and animal virus. The animal viruses that can be used as vectors, include, but are not limited to, retrovirus (including lentivirus), adenovirus, adeno-associated virus, herpes virus (such as herpes simplex virus), pox virus, baculovirus, papillomavirus, papova virus (such as SV40). A vector may comprise multiple elements for controlling expression, including, but not limited to, a promoter sequence, a transcription initiation sequence, an enhancer sequence, a selection element and a reporter gene. In addition, a vector may comprise origin of replication.

The term "host cell," as used herein, refers to a cellular system which can be engineered to generate proteins, protein fragments, or peptides of interest. Host cells include, without limitation, cultured cells, e.g., mammalian cultured cells derived from rodents (rats, mice, guinea pigs, or hamsters) such as CHO, BHK, NSO, SP2/0, YB2/0; or human tissues or hybridoma cells, yeast cells, and insect cells, and cells comprised within a transgenic animal or cultured tissue. The term encompasses not only the particular subject cell but also the progeny of such a cell. Because certain modifications may occur in succeeding generations due to either mutation or environmental influences, such progeny may not be identical to the parent cell, but are still included within the scope of the term "host cell."

The term "identity," as used herein, refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al, 1988, SIAMJ. Applied Math. 48:1073.

The term "immunogenicity," as used herein, refers to ability of stimulating the formation of specific antibodies or sensitized lymphocytes in organisms. It not only refers to the property of an antigen to stimulate a specific immunocyte to activate, proliferate and differentiate so as to finally generate immunologic effector substance such as antibody and sensitized lymphocyte, but also refers to the specific immune response that antibody or sensitized T lymphocyte can be formed in immune system of an organism after stimulating the organism with an antigen. Immunogenicity is the most important property of an antigen. Whether an antigen can successfully induce the generation of an immune response in a host depends on three factors, properties of an antigen, reactivity of a host, and immunization means.

The term "transfection," as used herein, refers to the process by which nucleic acids are introduced into eukaryoticcells, particularly mammalian cells. Protocols and techniques for transfection include but not limited to lipid transfection and chemical and physical methods such as electroporation. A number of transfection techniques are well known in the art and are disclosed herein. See, e.g., Graham et al., 1973, Virology 52:456; Sambrook et al., 2001, Molecular Cloning: A Laboratory Manual, supra; Davis et al., 1986, Basic Methods in Molecular Biology, Elsevier; Chu et al, 1981, Gene 13:197.

The term "hybridoma" and the term "hybridoma cell line," as used herein, may be used interchangeably. When the term "hybridoma" and the term "hybridoma cell line" are mentioned, they also include subclone and progeny cell of hybridoma.

The term "SPR" or "surface plasmon resonance," as used herein, refers to and includes an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 5 and Jönsson, U., et al. (1993) Ann. Biol. Clin. 51:19-26; Jönsson, U., et al. (1991) Biotechniques 11:620-627; Johnsson, B., et al. (1995) J. Mol. Recognit. 8:125-131; and Johnnson, B., et al. (1991) Anal. Biochem. 198:268-277.

The term "fluorescence-activated cell sorting" or "FACS," as used herein, refers to a specialized type of flow cytometry. It provides a method for sorting a heterogeneous mixture of biological cells into two or more containers, one cell at a time, based upon the specific light scattering and fluorescent characteristics of each cell (FlowMetric. "Sorting Out Fluorescence Activated Cell Sorting". Retrieved 2017-11-09.). Instruments for carrying out FACS are known to those of skill in the art and are commercially available to the public. Examples of such instruments include FACS Star Plus, FACScan and FACSort instruments from Becton Dickinson (Foster City, Calif.) Epics C from Coulter Epics Division (Hialeah, Fla.) and MoFlo from Cytomation (Colorado Springs, Colo.).

The term "antibody-dependent cell-mediated cytotoxicity" or "ADCC," as used herein, refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. PNAS (USA) 95:652-656 (1998).

The term "complement dependent cytotoxicity" or "CDC" refers to the lysis of a target cell in the presence of complement. Activation of the classical complement pathway is initiated by the binding of the first component of the complement system (Clq) to antibodies (of the appropriate subclass) which are bound to their cognate antigen. To assess complement activation, a CDC assay, e.g. as described in Gazzano-Santoro et al., J. Immunol. Methods 202: 163 (1996), may be performed.

The term "EU numbering" refers to the EU numbering as in Kabat et al. The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). Unless stated otherwise herein, references to residue numbers in the constant domain of antibodies means residue numbering by the EU numbering system. In certain embodiments, the antibodies as disclosed herein comprise Fc modifications, e.g., a mutation of serine ("S") to proline ("P") at position 228 of the amino acid sequence of human IgG4 Fc region, according to EU numbering.

The term "subject" includes any human or nonhuman animal, preferably humans.

The term "cancer," as used herein, refers to any or a tumor or a malignant cell growth, proliferation or metastasis-mediated, solid tumors and non-solid tumors such as leukemia and initiate a medical condition.

The term "treatment," "treating" or "treated," as used herein in the context of treating a condition, pertains generally to treatment and therapy, whether of a human or an animal, in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included. For cancer, "treating" may refer to dampen or slow the tumor or malignant cell growth, proliferation, or metastasis, or some combination thereof. For tumors, "treatment" includes removal of all or part of the tumor, inhibiting or slowing tumor growth and metastasis, preventing or delaying the development of a tumor, or some combination thereof.

The term "an effective amount," or "a therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen. For instance, the "an effective amount," when used in connection with treatment of target antigen-related diseases or conditions, refers to an antibody or antigen-binding portion thereof in an amount or concentration effective to treat the said diseases or conditions.

The term "prevent," "prevention" or "preventing," as used herein, with reference to a certain disease condition in a mammal, refers to preventing or delaying the onset of the disease, or preventing the manifestation of clinical or sub-clinical symptoms thereof.

The term "pharmaceutically acceptable," as used herein, means that the vehicle, diluent, excipient and/or salts thereof, are chemically and/or physically is compatible with other ingredients in the formulation, and the physiologically compatible with the recipient.

As used herein, the term "a pharmaceutically acceptable carrier and/or excipient" refers to a carrier and/or excipient pharmacologically and/or physiologically compatible with a subject and an active agent, which is well known in the art (see, e.g., Remington's Pharmaceutical Sciences. Edited by Gennaro AR, 19th ed. Pennsylvania: Mack Publishing Company, 1995), and includes, but is not limited to pH adjuster, surfactant, adjuvant and ionic strength enhancer. For example, the pH adjuster includes, but is not limited to, phosphate buffer; the surfactant includes, but is not limited to, cationic, anionic, or non-ionic surfactant, e.g., Tween-80; the ionic strength enhancer includes, but is not limited to, sodium chloride.

As used herein, the term "adjuvant" refers to a non-specific immunopotentiator, which can enhance immune response to an antigen or change the type of immune response in an organism when it is delivered together with the antigen to the organism or is delivered to the organism in advance. There are a variety of adjuvants, including, but not limited to, aluminium adjuvants (for example, aluminum hydroxide), Freund's adjuvants (for example, Freund's complete adjuvant and Freund's incomplete adjuvant), coryne bacterium *parvum*, lipopolysaccharide, cytokines, and the like. Freund's adjuvant is the most commonly used adjuvant in animal experiments now. Aluminum hydroxide adjuvant is more commonly used in clinical trials.

I. Anti-CD47 Antibodies

In some aspects, the present disclosure comprises an anti-CD47 antibody or an antigen-binding portion thereof.

In the context of the application, the "antibody" may include polyclonal antibodies, multiclonal antibodies, monoclonal antibodies, chimeric antibodies, humanized and primatized antibodies, CDR grafted antibodies, human antibodies, recombinantly produced antibodies, intrabodies, multispecific antibodies, bispecific antibodies, monovalent antibodies, multivalent antibodies, anti-idiotypic antibodies, synthetic antibodies, including muteins and variants thereof; and derivatives thereof including Fc fusions and other modifications, and any other immune-reactive molecule so long as it exhibits preferential association or binding with CD47. Moreover, unless dictated otherwise by contextual constraints the term further comprises all classes of antibodies (i.e. IgA, IgD, IgE, IgG, and IgM) and all subclasses (i.e., IgG1, IgG2, IgG3, IgG4, IgA1, and IgA2). In some preferred embodiments, the antibody is a monoclonal antibody. In more preferred embodiments, the antibody is a fully human monoclonal antibody.

Monoclonal antibodies can be prepared using a wide variety of techniques known in the art including hybridoma techniques, recombinant techniques, phage display technologies, transgenic animals (e.g., a XenoMouse®) or some combination thereof. For example, monoclonal antibodies can be produced using hybridoma and art-recognized biochemical and genetic engineering techniques such as described in more detail in An, Zhigiang (ed.) *Therapeutic Monoclonal Antibodies: From Bench to Clinic*, John Wiley and Sons, $1^{st}$ ed. 2009; Shire et. al. (eds.) *Current Trends in Monoclonal Antibody Development and Manufacturing*, Springer Science+Business Media LLC, $1^{st}$ ed. 2010; Harlow et al., *Antibodies: A Laboratory Manual*, Cold Spring Harbor Laboratory Press, 2nd ed. 1988; Hammerling, et al., in: *Monoclonal Antibodies and T-Cell Hybridomas* 563-681 (Elsevier, N.Y., 1981) each of which is incorporated herein in its entirety by reference. It should be understood that a selected binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also an antibody of the present disclosure. In some embodiments, the anti-human CD47 monoclonal antibody is prepared by using hybridoma techniques. Generation of hybridomas is well-known in the art. See, e.g., Harlow and Lane (1988) Antibodies, A Laboratory Manual, Cold Spring Harbor Publications, New York.

Properties of the Anti-CD47 Antibodies

The antibodies of the present disclosure are characterized by particular functional features or properties of the antibodies. In some embodiments, the isolated antibody or the antigen-binding portion thereof has one or more of the following properties:

(a) specifically binding to human CD47 and cynomolgus monkey CD47, expressed either as soluble proteins or on cell surfaces;

(b) effectively blocking the binding of CD47 to SIRPα, e.g. with an inhibitory rate >85%;

(c) weak binding to red blood cells (RBCs) and avoid inducing hemagglutination of human RBCs;

(d) inducing potent macrophage-mediated phagocytosis of tumor cells with reduced phagocytosis of human RBCs;

(e) inducing weak or no ADCC and CDC activity on tumor cells;

(f) having good thermal stability and being stable in human serum;

(g) inducing potent tumor growth inhibition in vivo in animal tumor models; and (h) exhibiting a synergic effect when administered in combination with other anti-tumor molecules, especially panitumumab.

Specific Binding to CD47

The antibody of the present disclosure binds to both human and cynomolgus monkey CD47 with high affinity. The binding of an antibody of the present disclosure to CD47 can be assessed using one or more techniques well established in the art, for instance, ELISA. The binding specificity of an antibody of the present disclosure can also be determined by monitoring binding of the antibody to cells expressing a CD47 protein, e.g., flow cytometry. For example, an antibody can be tested by a flow cytometry assay in which the antibody is reacted with a cell line that expresses human CD47, such as CHO or CHOK1 cells that have been transfected to express CD47 on their cell surface. Additionally, or alternatively, the binding of the antibody, including the binding kinetics (e.g., $K_d$ value) can be tested in BIAcore binding assays. Still other suitable binding assays include ELISA assays, for example using a recombinant CD47 protein.

In certain embodiments, an antibody of the present disclosure binds to a human CD47 at an EC50 of no more than 0.1 nM, no more than 0.09 nM, no more than 0.08 nM, no more than 0.07 nM, no more than 0.06 nM, no more than 0.05 nM, or more preferably no more than 0.04 nM, as determined by ELISA. In certain embodiments, an antibody of the present disclosure binds to a human CD47 with a $K_D$ of $1\times10^{-9}$ M or less, binds to a human CD47 with a $K_D$ of $5\times10^{-10}$ M or less, binds to a human CD47 with a $K_D$ of $1\times10^{-10}$ M or less, binds to a human CD47 with a $K_D$ of $5\times10^{-11}$ M or less, binds to a human CD47 with a $K_D$ of $4\times10^{-11}$ M or less, or more preferably binds to a human CD47 with a $K_D$ of $3\times10^{-11}$ M or less, as determined by SPR.

Blocking the Binding of CD47 to SIRPα

Signal regulatory protein alpha (SIRPα, also known as CD172a), which mainly expresses on the surface of macrophages, is a receptor for CD47. The antibodies of the present disclosure may modulate, e.g. block, inhibit, reduce, antagonize, neutralize or otherwise interfere with the binding of CD47 to signal regulatory protein alpha (SIRPα). CD47 is known to interact with SIRPα, and thus can escape immune surveillance. Blockade of a CD47-SIRPα interaction, e.g., using an anti-CD47 antibody as described herein may ameliorate or overcome the immune escape.

As demonstrated in the examples, the anti-CD47 antibodies described herein may effectively block the interaction of CD47 to SIRPα. In the present disclosure, an inhibitory rate can be obtained by comparing the OD450 values of the blocking sample comprising the anti-CD47 antibodies and a ligand only sample. A higher inhibitory rate corresponds to a higher blocking ability. For example, the inhibitory rate can be at least 70%, at least 75%, at least 80%, or at least 85%, i.e. the anti-CD47 antibodies may block at least 70%, at least 75%, at least 80%, or at least 85% of the interaction between CD47 and SIRPα in the absence of the anti-CD47 antibodies as disclosed herein.

Weak Binding to Human Red Blood Cells (RBCs) and Avoiding Hemagglutination of RBCs The ubiquitous expression of CD47, especially on the RBCs, limits the usage of anti-CD47 antibody therapy. Many anti-CD47 antibodies have been reported to cause hemagglutination of human red blood cells. In preclinical studies, transient hemolytic anemia was associated with anti-CD47 therapy due to elevated RBC clearance.

Surprisingly, the antibodies of the present disclosure only weakly bind to human red blood cells and avoid the undesirable effects of hemagglutination. As shown in the FACS assay in the examples, the IC50 value and Max MFI value of the antibodies as disclosed herein indicated a significantly lower binding to red blood cells compared to the benchmark anti-CD47 antibodies. In addition, the antibody or the antigen-binding portion herein could cause significantly less hemagglutination of human RBCs than a benchmark anti-CD47 antibody, for example, cause less than 90%, 80%, 70%, 60%, 50%, 40%, 30%, 20%, 10% or less hemagglutination of human RBCs compared to a benchmark anti-CD47 antibody. Exemplary benchmark antibodies include BMK1, BMK2 and BMK4 antibodies, as shown in Table 2.

Further, as demonstrated in the examples, administration of the antibodies herein in cynomolgus monkeys only causes a mild and transient dose-dependent anemia, which could spontaneously recover to normal baseline levels after a short period.

Inducing Potent Macrophage-Mediated Phagocytosis of Tumor Cells

When CD47 binds to SIRPα, the intracellular immunoreceptor tyrosine-based inhibitory motifs (ITIMs) of SIRPα is phosphorylated, followed by recruitment and activation of the tyrosine phosphatases such as SHP-1 and SHP-2. Then, the phosphoprotein substrates are dephosphorylated which affect downstream signaling pathways, transmitting a "don't eat me" signal to inhibit the macrophages' phagocytosis ability. Accumulating evidences have shown that CD47 was upregulated in many malignancies to evade the immune attack, and its overexpression was correlated with poor prognosis. Besides, interruption of the ligation of CD47 and SIRPα promotes the tumor cells to be phagocytosed by macrophages in various malignancies.

The antibodies of the disclosure are capable of inducing a potent phagocytosis of tumor cells. The tumor cells, as disclosed herein, encompass a wide variety of tumor cells, including tumor cells from hematological cancer or solid tumor. The hematological cancer can be selected from e.g. acute lymphoblastic leukemia (ALL), T-ALL, B-ALL, acute myelogenous leukemia (AML), Non-Hodgkin lymphoma, B-lymphoblastic leukemia/lymphoma; B-cell chronic lymphocytic leukemia, chronic lymphocytic leukemia (CLL), chronic myelocytic leukemia (CIVIL), Burkitt's lymphoma, follicular lymphoma, SLL, CNS lymphoma, Richter's Syndrome, multiple myeloma, and immunoblastic large cell lymphoma. The solid tumor can be selected from e.g. cancer of lung, pancreas, breast, liver, ovary, testicle, kidney, bladder, brain, cervix, colon/rectum, gastrointestinal tract, skin, prostate, and stomach etc.

Mediation of ADCC or CDC Activity

As described above, "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. "CDC" refers to the lysis of a target cell in the presence of complement.

It is found by the inventors that the antibodies of the present disclosure do not mediate ADCC or CDC activity on tumor cells, such as CCRF-CEM (acute lymphoblastic leukemia) cells or Raji cells.

Stability in Serum

Stability is also an important property of an antibody, particularly when it is used in therapeutics. It is found by the inventors that the antibodies of the present disclosure are stable for at least 14 days in human serum.

Inducing Potent Tumor Growth Inhibition

The assessment of tumor growth inhibition can be conducted by measuring a number of parameters, e.g. the body weight change, tumor volume, live imaging values correlated with tumor growth, animal survival time, etc. As shown in the examples, the antibodies as disclosed herein could achieve significant tumor growth inhibition in different tumor models.

Synergic Effect

Figure 18:
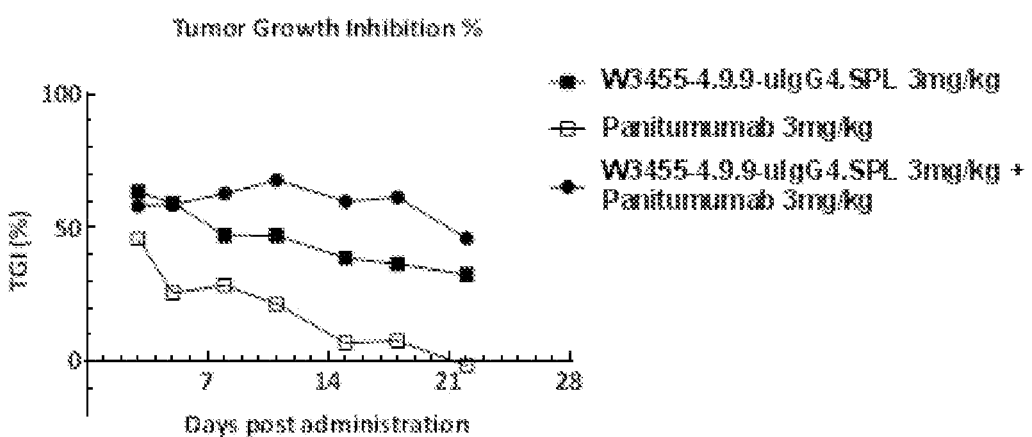
FIG. 18 shows the percentage of tumor growth inhibition (TGI) after administration of lead antibodyW3455 alone or in combination with panitumumab.

Surprisingly, the antibodies of the present disclosure exhibit a synergic effect when administered in combination with other anti-tumor molecules, especially panitumumab. The present disclosure has demonstrated that in the HT-29 colorectal adenocarcinoma model in NCG, the administration of a combination of the lead antibody W3455 and panitumumab achieved a significantly better tumor growth inhibition compared to W3455 or panitumumab alone (as shown in FIGS. 18 and 19).

CDRs of the Anti-CD47 Antibodies

In some embodiments, the isolated antibody or the antigen-binding portion thereof comprises:
A) one or more heavy chain CDRs (HCDRs) selected from the group consisting of:
  (i) a HCDR1 comprising SEQ ID NO: 1;
  (ii) a HCDR2 comprising SEQ ID NO: 2; and
  (iii) a HCDR3 comprising SEQ ID NO: 3;
B) one or more light chain CDRs (LCDRs) selected from the group consisting of:
  (i) a LCDR1 comprising SEQ ID NO: 4;
  (ii) a LCDR2 comprising SEQ ID NO: 5; and
  (iii) a LCDR3 comprising SEQ ID NO: 6; or
C) one or more HCDRs of A) and one or more LCDRs of B).

Variable regions and CDRs in an antibody sequence can be identified according to general rules that have been developed in the art (as set out above, such as, for example, the Kabat numbering system) or by aligning the sequences against a database of known variable regions. Methods for identifying these regions are described in Kontermann and Dubel, eds., Antibody Engineering, Springer, New York, N.Y., 2001 and Dinarello et al., Current Protocols in Immunology, John Wiley and Sons Inc., Hoboken, N.J., 2000. Exemplary databases of antibody sequences are described in, and can be accessed through, the "Abysis" website at www.bioinf.org.uk/abs (maintained by A. C. Martin in the Department of Biochemistry & Molecular Biology University College London, London, England) and the VBASE2 website at www.vbase2.org, as described in Retter et al., Nucl. Acids Res., 33 (Database issue): D671-D674 (2005). Preferably sequences are analyzed using the Abysis database, which integrates sequence data from Kabat, IMGT and the Protein Data Bank (PDB) with structural data from the PDB. See Dr. Andrew C. R. Martin's book chapter *Protein Sequence and Structure Analysis of Antibody Variable Domains.* In: *Antibody Engineering Lab Manual* (Ed.: Duebel, S. and Kontermann, R., Springer-Verlag, Heidelberg, ISBN-13: 978-3540413547, also available on the website bioinforg.uk/abs). The Abysis database website further includes general rules that have been developed for identifying CDRs which can be used in accordance with the teachings herein. Unless otherwise indicated, all CDRs set forth herein are derived according to Kabat numbering system.

In some specific embodiments, the isolated antibody or the antigen-binding portion thereof comprises a heavy chain variable region (VH) and a light chain variable region (VL), and wherein
(a) the VH comprises: a HCDR1 as set forth in SEQ ID NO: 1; a HCDR2 as set forth in SEQ ID NO: 2; and a HCDR3 as set forth in SEQ ID NO: 3; and
(b) the VL comprises: a LCDR1 as set forth in SEQ ID NO: 4; a LCDR2 as set forth in SEQ ID NO: 5; and a LCDR3 as set forth in SEQ ID NO: 6.

Variable Regions of the Anti-CD47 Antibodies

In some embodiments, the isolated antibody or the antigen-binding portion thereof comprises:
(A) a heavy chain variable region:
  (i) comprising the amino acid sequence of SEQ ID NO: 7;
  (ii) comprising an amino acid sequence at least 85%, 90%, or 95% identical to SEQ ID NO: 7; or
  (iii) comprising an amino acid sequence with addition, deletion and/or substitution of one or more amino acids compared with SEQ ID NO: 7; and/or
(B) a light chain variable region:
  (i) comprising the amino acid sequence of SEQ ID NO: 8;
  (ii) comprising an amino acid sequence at least 85%, at least 90%, or at least 95% identical to SEQ ID NO: 8; or
  (iii) comprising an amino acid sequence with addition, deletion and/or substitution of one or more amino acids compared with SEQ ID NO: 8.

The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present disclosure can further be used as a "query sequence" to perform a search against public databases to, for example, identify related sequences. Such searches can be performed using the XBLAST program (version 2.0) of Altschul, et al. (1990) *J. Mol. Biol.* 215:403-10. BLAST protein searches can be performed with the) (BLAST program, score=50, wordlength=3 to obtain amino acid sequences homologous to the antibody molecules of the present disclosure. To obtain gapped alignments for comparison purposes, Gapped BLAST can be utilized as described in Altschul et al, (1997) Nucleic Acids Res. 25(17):3389-3402. When utilizing BLAST and Gapped BLAST programs, the default parameters of the respective programs (e.g., XBLAST and NBLAST) can be used. See www.ncbi.nlm.nih.gov.

In some specific embodiments, the heavy chain variable region of the isolated antibody or the antigen-binding portion thereof is consisted of the amino acid sequence of SEQ ID NO: 7, and the light chain variable region of the isolated antibody or the antigen-binding portion thereof is consisted of the amino acid sequence of SEQ ID NO: 8.

In other embodiments, the amino acid sequences of the heavy chain variable region and/or the light chain variable region can be at least 85%, 86%, 87%, 88%, 89%, 90%, 91%, 92%, 93%, 94%, 95%, 96%, 97%, 98% or 99% identical to the respective sequences set forth above.

In some further embodiments, the isolated antibody or the antigen-binding portion thereof may contain conservative substitution or modification of amino acids in the variable regions of the heavy chain and/or light chain. It is understood in the art that certain conservative sequence modification can be made which do not remove antigen binding. See, e.g., Brummell et al. (1993) Biochem 32:1180-8; de Wildt et al. (1997) Prot. Eng. 10:835-41; Komissarov et al. (1997) J. Biol. Chem. 272:26864-26870; Hall et al. (1992) J. Immunol. 149:1605-12; Kelley and O'Connell (1993) Biochem. 32:6862-35; Adib-Conquy et al. (1998) Int. Immunol. 10:341-6 and Beers et al. (2000) Clin. Can. Res. 6:2835-43.

As described above, the term "conservative substitution," as used herein, refers to amino acid substitutions which would not disadvantageously affect or change the essential properties of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having alkaline side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, pro line, phenylalanine, methionine), amino acids having β-branched side chains (such as threonine, valine, isoleucine) and amino acids having aromatic side chains (for example, tyrosine, phenylalanine, tryptophan, histidine). Therefore, a corresponding amino acid residue is preferably substituted with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl. Acad. Sci. USA 94: 412-417 (1997), which are incorporated herein by reference).

Fc Region

Preferably, the Fc region of the antibodies as disclosed herein is human Fc region, such as a wild-type human Fc region or a variant thereof. The Fc region may be of any isotype, including, but not limited to, IgG1, IgG2, IgG3 or IgG4. In some embodiments, the Fc region is of the IgG4 isotype.

The Fc region variant may comprise one or more amino acid changes (e.g., insertions, deletions or substitutions) as compared to wild-type Fc region, without changing the desired functionality. For example, the disclosure includes antibodies comprising one or more modifications in the Fc region that results in a modified Fc region that may have a modified binding interaction (e.g., enhanced or diminished) between Fc and FcRn. Non-limiting examples of Fc modifications also include, e.g., a mutation of serine ("S") to proline ("P") at position 228 of the amino acid sequence of human IgG4 Fc region. The S228P mutation reduces Fab-arm exchange by stabilizing the disulfides in the core-hinge of the IgG4 molecules, thus belongs to an IgG4 stabilization mutation which helps prevent half-antibody formation.

II. Nucleic Acid Molecules Encoding the Anti-CD47 Antibodies

In some aspects, the present disclosure is directed to an isolated nucleic acid molecule, comprising a nucleic acid sequence encoding the heavy chain variable region and/or the light chain variable region of the isolated antibody as disclosed herein.

Nucleic acids of the present disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

The isolated nucleic acid encoding the VH region can be converted to a full-length heavy chain gene by operatively linking the VH-encoding nucleic acid to another DNA molecule encoding heavy chain constant regions (CH1, CH2 and CH3). The sequences of human heavy chain constant region genes are known in the art (see e.g., Kabat et al. (1991), supra) and DNA fragments encompassing these regions can be obtained by standard PCR amplification. The heavy chain constant region can be an IgG1, IgG2, IgG3, IgG4, IgA, IgE, IgM or IgD constant region, but more preferably is an IgG1 or IgG4 constant region.

The isolated nucleic acid encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat et al., supra) and DNA fragments encompassing these regions can be obtained by standard PCR amplification. In preferred embodiments, the light chain constant region can be a kappa or lambda constant region.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

In some embodiments, the present disclosure is directed to an isolated nucleic acid molecule, comprising a nucleic acid sequence encoding the heavy chain variable region of the isolated antibody as disclosed herein.

In some specific embodiments, the isolated nucleic acid molecule encodes the heavy chain variable region of the isolated antibody and comprises a nucleic acid sequence selected from the group consisting of:

(A) a nucleic acid sequence that encodes a heavy chain variable region as set forth in SEQ ID NO: 7;

(B) a nucleic acid sequence as set forth in SEQ ID NO: 9; or (C) a nucleic acid sequence that hybridized under high stringency conditions to the complementary strand of the nucleic acid sequence of (A) or (B).

In some embodiments, the present disclosure is directed to an isolated nucleic acid molecule, comprising a nucleic acid sequence encoding the light chain variable region of the isolated antibody as disclosed herein.

In some specific embodiments, the isolated nucleic acid molecule encodes the light chain variable region of the isolated antibody comprises a nucleic acid sequence selected from the group consisting of:

(A) a nucleic acid sequence that encodes a light chain variable region as set forth in SEQ ID NO: 8;
(B) a nucleic acid sequence as set forth in SEQ ID NO: 10; or
(C) a nucleic acid sequence that hybridized under high stringency conditions to the complementary strand of the nucleic acid sequence of (A) or (B).

For example, the nucleic acid molecule is consisted of SEQ ID NO: 9 or 10. Alternatively, the nucleic acid molecule share an at least 80% (e.g. at least 85%, 86%, 87%, 88%, 89%, 90%, 91%, 92%, 93%, 94%, 95%, 96%, 97%, 98%, or 99%) sequence identity to SEQ ID NO: 9 or 10. In some specific embodiments, the percentage of identity is derived from the degeneracy of the genetic code, and the encoded protein sequences remain unchanged.

Exemplary high stringency conditions include hybridization at 45° C. in 5×SSPE and 45% formamide, and a final wash at 65° C. in 0.1×SSC. It is understood in the art that conditions of equivalent stringency can be achieved through variation of temperature and buffer, or salt concentration as described Ausubel, et al. (Eds.), Protocols in Molecular Biology, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook, et al, (Eds.), Molecular Cloning: A laboratory Manual. Cold Spring Harbor Laboratory Press: Cold Spring Harbor, N.Y. (1989), pp. 9.47 to 9.51.

III. Host Cells

Host cells as disclosed in the present disclosure may be any cell which is suitable for expressing the antibodies of the present disclosure, for instance, mammalian cells. Mammalian host cells for expressing the antibodies of the present disclosure include Chinese Hamster Ovary (CHO cells) (including dhfr CHO cells, described in Urlaub and Chasin, (1980) Proc. Natl. Acad. ScL USA 77:4216-4220, used with a DHFR selectable marker, e.g., as described in R. J. Kaufman and P. A. Sharp (1982) J. Mol. Biol. 159:601-621), NSO myeloma cells, COS cells and SP2 cells. In particular, for use with NSO myeloma cells, another expression system is the GS gene expression system disclosed in WO 87/04462, WO 89/01036 and EP 338,841. When recombinant expression vectors encoding the antibody are introduced into mammalian host cells, the antibodies are produced by culturing the host cells for a period of time sufficient to allow for expression of the antibody in the host cells or, secretion of the antibody into the culture medium in which the host cells are grown. Antibodies can be recovered from the culture medium using standard protein purification methods.

IV. Pharmaceutical Compositions

In some aspects, the present disclosure is directed to a pharmaceutical composition comprising at least one antibody or antigen-binding portion thereof as disclosed herein and a pharmaceutically acceptable carrier.

Components of the Compositions

The pharmaceutical composition may optionally contain one or more additional pharmaceutically active ingredients, such as another antibody or a drug. The pharmaceutical compositions of the present disclosure also can be administered in a combination therapy with, for example, another immune-stimulatory agent, anti-cancer agent, an antiviral agent, or a vaccine, such that the anti-CD47 antibody enhances the immune response against the vaccine. A pharmaceutically acceptable carrier can include, for example, a pharmaceutically acceptable liquid, gel or solid carriers, an aqueous medium, a non-aqueous medium, an anti-microbial agent, isotonic agents, buffers, antioxidants, anesthetics, suspending/dispersing agent, a chelating agent, a diluent, adjuvant, excipient or a nontoxic auxiliary substance, other known in the art various combinations of components or more.

Suitable components may include, for example, antioxidants, fillers, binders, disintegrating agents, buffers, preservatives, lubricants, flavorings, thickening agents, coloring agents, emulsifiers or stabilizers such as sugars and cyclodextrin. Suitable anti-oxidants may include, for example, methionine, ascorbic acid, EDTA, sodium thiosulfate, platinum, catalase, citric acid, cysteine, mercapto glycerol, thioglycolic acid, Mercapto sorbitol, butyl methyl anisole, butylated hydroxy toluene and/or propylgalacte. As disclosed in the present disclosure, in a solvent containing an antibody or an antigen-binding fragment of the present disclosure discloses compositions include one or more anti-oxidants such as methionine, reducing antibody or antigen binding fragment thereof may be oxidized. The oxidation reduction may prevent or reduce a decrease in binding affinity, thereby enhancing antibody stability and extended shelf life. Thus, in some embodiments, the present disclosure provides a composition comprising one or more antibodies or antigen binding fragment thereof and one or more anti-oxidants such as methionine. The present disclosure further provides a variety of methods, wherein an antibody or antigen binding fragment thereof is mixed with one or more anti-oxidants, such as methionine, so that the antibody or antigen binding fragment thereof can be prevented from oxidation, to extend their shelf life and/or increased activity.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

Administration, Formulation and Dosage

The pharmaceutical composition of the present disclosure may be administered in vivo, to a subject in need thereof, by various routes, including, but not limited to, oral, intravenous, intra-arterial, subcutaneous, parenteral, intranasal, intramuscular, intracranial, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. The appropriate formulation and route of administration may be selected according to the intended application and therapeutic regimen.

Suitable formulations for enteral administration include hard or soft gelatin capsules, pills, tablets, including coated tablets, elixirs, suspensions, syrups or inhalations and controlled release forms thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Similarly, the particular dosage regimen, including dose, timing and repetition, will depend on the particular individual and that individual's medical history, as well as empirical considerations such as pharmacokinetics (e.g., half-life, clearance rate, etc.).

Frequency of administration may be determined and adjusted over the course of therapy, and is based on reducing the number of proliferative or tumorigenic cells, maintaining the reduction of such neoplastic cells, reducing the proliferation of neoplastic cells, or delaying the development of metastasis. In some embodiments, the dosage administered may be adjusted or attenuated to manage potential side effects and/or toxicity. Alternatively, sustained continuous release formulations of a subject therapeutic composition may be appropriate.

It will be appreciated by one of skill in the art that appropriate dosages can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action that achieve the desired effect without causing substantial harmful or deleterious side-effects.

In general, the antibody or the antigen binding portion thereof of the present disclosure may be administered in various ranges. These include about 5 µg/kg body weight to about 100 mg/kg body weight per dose; about 50 µg/kg body weight to about 5 mg/kg body weight per dose; about 100 µg/kg body weight to about 10 mg/kg body weight per dose. Other ranges include about 100 µg/kg body weight to about 20 mg/kg body weight per dose and about 0.5 mg/kg body weight to about 20 mg/kg body weight per dose. In certain embodiments, the dosage is at least about 100 µg/kg body weight, at least about 250 µg/kg body weight, at least about 750 µg/kg body weight, at least about 3 mg/kg body weight, at least about 5 mg/kg body weight, at least about 10 mg/kg body weight.

In any event, the antibody or the antigen binding portion thereof of the present disclosure is preferably administered as needed to a subject in need thereof. Determination of the frequency of administration may be made by persons skilled in the art, such as an attending physician based on considerations of the condition being treated, age of the subject being treated, severity of the condition being treated, general state of health of the subject being treated and the like.

In certain preferred embodiments, the course of treatment involving the antibody or the antigen-binding portion thereof of the present disclosure will comprise multiple doses of the selected drug product over a period of weeks or months. More specifically, the antibody or the antigen-binding portion thereof of the present disclosure may be administered once every day, every two days, every four days, every week, every ten days, every two weeks, every three weeks, every month, every six weeks, every two months, every ten weeks or every three months. In this regard, it will be appreciated that the dosages may be altered or the interval may be adjusted based on patient response and clinical practices.

Dosages and regimens may also be determined empirically for the disclosed therapeutic compositions in individuals who have been given one or more administration(s). For example, individuals may be given incremental dosages of a therapeutic composition produced as described herein. In selected embodiments, the dosage may be gradually increased or reduced or attenuated based respectively on empirically determined or observed side effects or toxicity. To assess efficacy of the selected composition, a marker of the specific disease, disorder or condition can be followed as described previously. For cancer, these include direct measurements of tumor size via palpation or visual observation, indirect measurement of tumor size by x-ray or other imaging techniques; an improvement as assessed by direct tumor biopsy and microscopic examination of the tumor sample; the measurement of an indirect tumor marker (e.g., PSA for prostate cancer) or a tumorigenic antigen identified according to the methods described herein, a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of neoplastic condition, the stage of neoplastic condition, whether the neoplastic condition has begun to metastasize to other location in the individual, and the past and concurrent treatments being used.

Compatible formulations for parenteral administration (e.g., intravenous injection) will comprise the antibody or antigen-binding portion thereof as disclosed herein in concentrations of from about 10 µg/ml to about 100 mg/ml. In certain selected embodiments, the concentrations of the antibody or the antigen binding portion thereof will comprise 20 µg/ml, 40 µg/ml, 60 µg/ml, 80 µg/ml, 100 µg/ml, 200 µg/ml, 300, µg/ml, 400 µg/ml, 500 µg/ml, 600 µg/ml, 700 µg/ml, 800 µg/ml, 900 µg/ml or 1 mg/ml. In other preferred embodiments, the concentrations of the antibody or the antigen binding portion thereof will comprise 2 mg/ml, 3 mg/ml, 4 mg/ml, 5 mg/ml, 6 mg/ml, 8 mg/ml, 10 mg/ml, 12 mg/ml, 14 mg/ml, 16 mg/ml, 18 mg/ml, 20 mg/ml, 25 mg/ml, 30 mg/ml, 35 mg/ml, 40 mg/ml, 45 mg/ml, 50 mg/ml, 60 mg/ml, 70 mg/ml, 80 mg/ml, 90 mg/ml or 100 mg/ml.

V. Applications/Indications

The antibodies, antibody compositions and methods of the present disclosure have numerous in vitro and in vivo utilities involving, for example, detection of CD47 or enhancement of immune response. For example, these molecules can be administered to cells in culture, in vitro or ex vivo, or to human subjects, e.g., in vivo, to enhance immunity in a variety of situations. The immune response can be modulated, for instance, augmented, stimulated or up-regulated.

For instance, the subjects include human patients in need of enhancement of an immune response. The methods are particularly suitable for treating human patients having a disorder that can be treated by augmenting an immune response (e.g., the T-cell mediated immune response). In a particular embodiment, the methods are particularly suitable for treatment of cancer in vivo. To achieve antigen-specific enhancement of immunity, the anti-CD47 antibodies can be administered together with an antigen of interest or the antigen may already be present in the subject to be treated (e.g., a tumor-bearing or virus-bearing subject). When antibodies to CD47 are administered together with another agent, the two can be administered in either order or simultaneously.

The present disclosure further provides methods for detecting the presence of human CD47 antigen in a sample, or measuring the amount of human CD47 antigen, comprising contacting the sample, and a control sample, with a human monoclonal antibody, or an antigen binding portion thereof, which specifically binds to human CD47, under conditions that allow for formation of a complex between the antibody or portion thereof and human CD47. The formation of a complex is then detected, wherein a difference complex formation between the sample compared to the control sample is indicative of the presence of human CD47 antigen in the sample. Moreover, the anti-CD47 antibodies of the present disclosure can be used to purify human CD47 via immunoaffinity purification.

Treatment of Disorders Including Cancers

In some aspects, the present disclosure provides a method of treating a disorder or a disease in a mammal, which comprises administering to the subject (for example, a human) in need of treatment a therapeutically effective amount of the antibody or antigen-binding portion thereof as disclosed herein. The disorder or disease comprises but not limited to, proliferative disorders (such as cancers). For example, the disorder may be a cancer.

A variety of cancers, whether malignant or benign and whether primary or secondary, may be treated or prevented with a method provided by the disclosure. The cancers may be solid cancers or hematologic malignancies. Examples of such cancers include lung cancers such as bronchogenic carcinoma (e.g., non-small cell lung cancer, squamous cell carcinoma, small cell carcinoma, large cell carcinoma, and adenocarcinoma), alveolar cell carcinoma, bronchial adenoma, chondromatous hamartoma (noncancerous), and sarcoma (cancerous); heart cancer such as myxoma, fibromas, and rhabdomyomas; bone cancers such as osteochondromas, condromas, chondroblastomas, chondromyxoid fibromas, osteoid osteomas, giant cell tumors, chondrosarcoma, multiple myeloma, osteosarcoma, fibrosarcomas, malignant fibrous histiocytomas, Ewing's tumor (Ewing's sarcoma), and reticulum cell sarcoma; brain cancer such as gliomas (e.g., glioblastoma multiforme), anaplastic astrocytomas, astrocytomas, oligodendrogliomas, medulloblastomas, chordoma, Schwannomas, ependymomas, meningiomas, pituitary adenoma, pinealoma, osteomas, hemangioblastomas, craniopharyngiomas, chordomas, germinomas, teratomas, dermoid cysts, and angiomas; cancers in digestive system such as colon cancer, leiomyoma, epidermoid carcinoma, adenocarcinoma, leiomyosarcoma, stomach adenocarcinomas, intestinal lipomas, intestinal neurofibromas, intestinal fibromas, polyps in large intestine, and colorectal cancers; liver cancers such as hepatocellular adenomas, hemangioma, hepatocellular carcinoma, fibrolamellar carcinoma, cholangiocarcinoma, hepatoblastoma, and angiosarcoma; kidney cancers such as kidney adenocarcinoma, renal cell carcinoma, hypernephroma, and transitional cell carcinoma of the renal pelvis; bladder cancers; hematological cancers such as acute lymphocytic (lymphoblastic) leukemia, acute myeloid (myelocytic, myelogenous, myeloblasts, myelomonocytic) leukemia, chronic lymphocytic leukemia (e.g., Sezary syndrome and hairy cell leukemia), chronic myelocytic (myeloid, myelogenous, granulocytic) leukemia, Hodgkin's lymphoma, non-Hodgkin's lymphoma, B cell lymphoma, mycosis fungoides, and myeloproliferative disorders (including myeloproliferative disorders such as polycythemia vera, myelofibrosis, thrombocythemia, and chronic myelocytic leukemia); skin cancers such as basal cell carcinoma, squamous cell carcinoma, melanoma, Kaposi's sarcoma, and Paget's disease; head and neck cancers; eye-related cancers such as retinoblastoma and intraoccular melanocarcinoma; male reproductive system cancers such as benign prostatic hyperplasia, prostate cancer, and testicular cancers (e.g., seminoma, teratoma, embryonal carcinoma, and choriocarcinoma); breast cancer; female reproductive system cancers such as uterine cancer (endometrial carcinoma), cervical cancer (cervical carcinoma), cancer of the ovaries (ovarian carcinoma), vulvar carcinoma, vaginal carcinoma, fallopian tube cancer, and hydatidiform mole; thyroid cancer (including papillary, follicular, anaplastic, or medullary cancer); pheochromocytomas (adrenal gland); noncancerous growths of the parathyroid glands; pancreatic cancers; and hematological cancers such as leukemias, myelomas, non-Hodgkin's lymphomas, and Hodgkin's lymphomas. In some specific embodiments, the cancer is colon cancer.

In some embodiments, examples of cancer include but not limited to B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), B-cell proliferative disorders, and Meigs' syndrome. More specific examples include, but are not limited to, relapsed or refractory NHL, front line low grade NHL, Stage III/IV NHL, chemotherapy resistant NHL, precursor B lymphoblastic leukemia and/or lymphoma, small lymphocytic lymphoma, B-cell chronic lymphocytic leukemia and/or prolymphocytic leukemia and/ or small lymphocytic lymphoma, B-cell prolymphocytic lymphoma, immunocytoma and/or lymphoplasmacytic lymphoma, lymphoplasmacytic lymphoma, marginal zone B-cell lymphoma, splenic marginal zone lymphoma, extranodal marginal zone-MALT lymphoma, nodal marginal zone lymphoma, hairy cell leukemia, plasmacytoma and/or plasma cell myeloma, low grade/follicular lymphoma, intermediate grade/follicular NHL, mantle cell lymphoma, follicle center lymphoma (follicular), intermediate grade diffuse NHL, diffuse large B-cell lymphoma, aggressive NHL (including aggressive front-line NHL and aggressive relapsed NHL), NHL relapsing after or refractory to autologous stem cell transplantation, primary mediastinal large B-cell lymphoma, primary effusion lymphoma, high grade immunoblastic NHL, high grade lymphoblastic NHL, high grade small non-cleaved cell NHL, bulky disease NHL, Burkitt's lymphoma, precursor (peripheral) large granular lymphocytic leukemia, mycosis fungoides and/or Sezary syndrome, skin (cutaneous) lymphomas, anaplastic large cell lymphoma, angiocentric lymphoma.

In some embodiments, examples of cancer further include, but are not limited to, B-cell proliferative disorders, which further include, but are not limited to, lymphomas (e.g., B-Cell Non-Hodgkin's lymphomas (NHL)) and lymphocytic leukemias. Such lymphomas and lymphocytic leukemias include e.g. a) follicular lymphomas, b) Small Non-Cleaved Cell Lymphomas/Burkitt's lymphoma (including endemic Burkitt's lymphoma, sporadic Burkitt's lymphoma and Non-Burkitt's lymphoma), c) marginal zone lymphomas (including extranodal marginal zone B-cell lymphoma (Mucosa-associated lymphatic tissue lymphomas, MALT), nodal marginal zone B-cell lymphoma and splenic marginal zone lymphoma), d) Mantle cell lymphoma (MCL), e) Large Cell Lymphoma (including B-cell diffuse large cell lymphoma (DLCL), Diffuse Mixed Cell Lymphoma, Immunoblastic Lymphoma, Primary Mediastinal B-Cell Lymphoma, Angiocentric Lymphoma-Pulmonary B-Cell Lymphoma), f) hairy cell leukemia, g) lymphocytic lymphoma, Waldenstrom's macroglobulinemia, h) acute lymphocytic leukemia (ALL), chronic lymphocytic leukemia (CLL)/small lymphocytic lymphoma (SLL), B cell prolymphocytic leukemia, i) plasma cell neoplasms, plasma cell myeloma, multiple myeloma, plasmacytoma, and/or j) Hodgkin's disease.

In some other embodiments, the disorder is an autoimmune disease. Examples of autoimmune diseases that may be treated with the antibody or antigen-binding portion thereof include autoimmune encephalomyelitis, lupus erythematosus, and rheumatoid arthritis. The antibody or the antigen-binding portion thereof may also be used to treat or preventinfectious disease, inflammatory disease (such as allergic asthma) and chronic graft-versus-host disease.

Stimulation of an Immune Response

In some aspects, the present disclosure also provides a method of enhancing (for example, stimulating) an immune response in a subject comprising administering an antibody or an antigen binding portion thereof of the present disclosure to the subject such that an immune response in the subject is enhanced. For example, the subject is a mammal. In some specific embodiments, the subject is a human.

The term "enhancing an immune response" or its grammatical variations, means stimulating, evoking, increasing, improving, or augmenting any response of a mammal's immune system. The immune response may be a cellular response (i.e. cell-mediated, such as cytotoxic T lymphocyte mediated) or a humoral response (i.e. antibody mediated response), and may be a primary or secondary immune response. Examples of enhancement of immune response include increased $CD4^+$ helper T cell activity and generation of cytolytic T cells. The enhancement of immune response can be assessed using a number of in vitro or in vivo measurements known to those skilled in the art, including, but not limited to, cytotoxic T lymphocyte assays, release of cytokines (for example IL-2 production or IFN-γ production), regression of tumors, survival of tumor bearing animals, antibody production, immune cell proliferation, expression of cell surface markers, and cytotoxicity. Typically, methods of the disclosure enhance the immune response by a mammal when compared to the immune response by an untreated mammal or a mammal not treated using the methods as disclosed herein. In some embodiments, the antibody or an antigen binding portion thereof is used to enhance the immune response of a human to a microbial pathogen (such as a virus). In another embodiment, the antibody or an antigen binding portion thereof is used to enhance the immune response of a human to a vaccine. In some embodiments, the method enhances a cellular immune response, particularly a cytotoxic T cell response. In another embodiment, the cellular immune response is a T helper cell response. In still another embodiment, the immune response is a cytokine production, particularly IFN-γ production or IL-2 production. The antibody or an antigen binding portion thereof may be used to enhance the immune response of a human to a microbial pathogen (such as a virus) or to a vaccine.

The antibody or the antigen-binding portion thereof may be used alone as a monotherapy, or may be used in combination with chemical therapies or radiotherapies.

Combined Use with Chemotherapies

The antibody or the antigen-binding portion thereof may be used in combination with an anti-cancer agent, a cytotoxic agent or chemotherapeutic agent.

The term "anti-cancer agent" or "anti-proliferative agent" means any agent that can be used to treat a cell proliferative disorder such as cancer, and includes, but is not limited to, cytotoxic agents, cytostatic agents, anti-angiogenic agents, debulking agents, chemotherapeutic agents, radiotherapy and radiotherapeutic agents, targeted anti-cancer agents, BRMs, therapeutic antibodies, cancer vaccines, cytokines, hormone therapies, radiation therapy and anti-metastatic agents and immunotherapeutic agents. It will be appreciated that, in selected embodiments as discussed above, such anti-cancer agents may comprise conjugates and may be associated with the disclosed site-specific antibodies prior to administration. More specifically, in certain embodiments selected anti-cancer agents will be linked to the unpaired cysteines of the engineered antibodies to provide engineered conjugates as set forth herein. Accordingly, such engineered conjugates are expressly contemplated as being within the scope of the present disclosure. In other embodiments, the disclosed anti-cancer agents will be given in combination with site-specific conjugates comprising a different therapeutic agent as set forth above.

As used herein the term "cytotoxic agent" means a substance that is toxic to the cells and decreases or inhibits the function of cells and/or causes destruction of cells. In certain embodiments, the substance is a naturally occurring molecule derived from a living organism. Examples of cytotoxic agents include, but are not limited to, small molecule toxins or enzymatically active toxins of bacteria (e.g., Diptheria toxin, *Pseudomonas* endotoxin and exotoxin, Staphylococcal enterotoxin A), fungal (e.g., α-sarcin, restrictocin), plants (e.g., abrin, ricin, modeccin, viscumin, pokeweed anti-viral protein, saporin, gelonin, momoridin, trichosanthin, barley toxin, *Aleurites fordii* proteins, dianthin proteins, *Phytolacca* mericana proteins (PAPI, PAPII, and PAP-S), *Momordica charantia* inhibitor, curcin, crotin, *Saponaria officinalis* inhibitor, gelonin, mitegellin, restrictocin, phenomycin, neomycin, and the tricothecenes) or animals, (e.g., cytotoxic RNases, such as extracellular pancreatic RNases; DNase I, including fragments and/or variants thereof).

For the purposes of the present disclosure a "chemotherapeutic agent" comprises a chemical compound that non-specifically decreases or inhibits the growth, proliferation, and/or survival of cancer cells (e.g., cytotoxic or cytostatic agents). Such chemical agents are often directed to intracellular processes necessary for cell growth or division, and are thus particularly effective against cancerous cells, which generally grow and divide rapidly. For example, vincristine depolymerizes microtubules, and thus inhibits cells from entering mitosis. In general, chemotherapeutic agents can include any chemical agent that inhibits, or is designed to inhibit, a cancerous cell or a cell likely to become cancerous or generate tumorigenic progeny (e.g., TIC). Such agents are often administered, and are often most effective, in combination, e.g., in regimens such as CHOP or FOLFIRI.

Examples of anti-cancer agents that may be used in combination with the site-specific constructs of the present disclosure (either as a component of a site specific conjugate or in an unconjugated state) include, but are not limited to, alkylating agents, alkyl sulfonates, aziridines, ethylenimines and methylamelamines, acetogenins, a camptothecin, bryostatin, callystatin, CC-1065, cryptophycins, dolastatin, duocarmycin, eleutherobin, pancratistatin, a sarcodictyin, spongistatin, nitrogen mustards, antibiotics, enediyne antibiotics, dynemicin, bisphosphonates, esperamicin, chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, erlotinib, vemurafenib, crizotinib, sorafenib, ibrutinib, enzalutamide, folic acid analogues, purine analogs, androgens, anti-adrenals, folic acid replenisher such as frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, an epothilone, etoglucid, gallium nitrate, hydroxyurea, lentinan, lonidainine, maytansinoids, mitoguazone, mitoxantrone, mopidanmol, nitraerine, pentostatin, phenamet, pirarubicin, losoxantrone, podophyllinic acid, 2-ethylhydrazide, procarbazine, PSK® polysaccharide complex (JHS Natural Products, Eugene, Oreg.), razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, chloranbucil; GEMZAR® gemcitabine; 6-thioguanine; mercaptopurine; methotrexate; platinum analogs, vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11), topoisomerase inhibitor RFS 2000; difluorometlhylornithine; retinoids; capecitabine; combretastatin; leucovorin; oxaliplatin; inhibitors of PKC-alpha, Raf, H-Ras, EGFR and VEGF-A that reduce cell proliferation and pharmaceutically acceptable salts, acids or derivatives of any of the above. Also included in this definition are anti-hormonal agents that act to regulate or inhibit hormone action on tumors such as anti-estrogens and selective estrogen receptor modulators, aromatase inhibitors that inhibit the enzyme aromatase, which regulates estrogen production in the adrenal glands, and anti-androgens; as well as troxacitabine (a 1,3-dioxolane nucleoside cytosine analog); antisense oligonucleotides, ribozymes such as a VEGF expression inhibitor and a HER2 expression inhibitor; vaccines, PROLEUKIN® rIL-2; LURTOTECAN® topoisomerase 1 inhibitor; ABARELIX® rmRH; Vinorelbine and Esperamicins and pharmaceutically acceptable salts, acids or derivatives of any of the above.

Combined Use with Radiotherapies

The present disclosure also provides for the combination of the antibody or the antigen-binding portion thereof with radiotherapy (i.e., any mechanism for inducing DNA damage locally within tumor cells such as gamma-irradiation, X-rays, UV-irradiation, microwaves, electronic emissions and the like). Combination therapy using the directed delivery of radioisotopes to tumor cells is also contemplated, and the disclosed conjugates may be used in connection with a targeted anti-cancer agent or other targeting means. Typically, radiation therapy is administered in pulses over a period of time from about 1 to about 2 weeks. The radiation therapy may be administered to subjects having head and neck cancer for about 6 to 7 weeks. Optionally, the radiation therapy may be administered as a single dose or as multiple, sequential doses.

VI. Pharmaceutical Packs and Kits

Pharmaceutical packs and kits comprising one or more containers, comprising one or more doses of the antibody or the antigen-binding portion thereof are also provided. In certain embodiments, a unit dosage is provided wherein the unit dosage contains a predetermined amount of a composition comprising, for example, the antibody or the antigen-binding portion thereof, with or without one or more additional agents. For other embodiments, such a unit dosage is supplied in single-use prefilled syringe for injection. In still other embodiments, the composition contained in the unit dosage may comprise saline, sucrose, or the like; a buffer, such as phosphate, or the like; and/or be formulated within a stable and effective pH range. Alternatively, in certain embodiments, the composition may be provided as a lyophilized powder that may be reconstituted upon addition of an appropriate liquid, for example, sterile water or saline solution. In certain preferred embodiments, the composition comprises one or more substances that inhibit protein aggregation, including, but not limited to, sucrose and arginine. Any label on, or associated with, the container(s) indicates that the enclosed conjugate composition is used for treating the neoplastic disease condition of choice.

The present disclosure also provides kits for producing single-dose or multi-dose administration units of antibodies and, optionally, one or more anti-cancer agents. The kit comprises a container and a label or package insert on or associated with the container. Suitable containers include, for example, bottles, vials, syringes, etc. The containers may be formed from a variety of materials such as glass or plastic and contain a pharmaceutically effective amount of the disclosed antibodies or antigen-binding portion thereof. In other preferred embodiments, the container(s) comprise a sterile access port (for example the container may be an intravenous solution bag or a vial having a stopper pierceable by a hypodermic injection needle). Such kits will generally contain in a suitable container a pharmaceutically acceptable formulation of the antibodies and, optionally, one or more anti-cancer agents in the same or different containers. The kits may also contain other pharmaceutically acceptable formulations, either for diagnosis or combined therapy. For example, in addition to the antibody or the antigen-binding portion thereof of the present disclosure such kits may contain any one or more of a range of anti-cancer agents such as chemotherapeutic or radiotherapeutic drugs; anti-angiogenic agents; anti-metastatic agents; targeted anti-cancer agents; cytotoxic agents; and/or other anti-cancer agents.

More specifically the kits may have a single container that contains the disclosed antibody or the antigen-binding portion thereof, with or without additional components, or they may have distinct containers for each desired agent. Alternatively, the antibodies and any optional anti-cancer agent of the kit may be maintained separately within distinct containers prior to administration to a patient. The kits may also comprise a second/third container means for containing a sterile, pharmaceutically acceptable buffer or other diluents such as bacteriostatic water for injection (BWFI), phosphate-buffered saline (PBS), Ringer's solution and dextrose solution.

When the components of the kit are provided in one or more liquid solutions, the liquid solution is preferably an aqueous solution, with a sterile aqueous or saline solution being particularly preferred. However, the components of the kit may be provided as dried powder(s). When reagents or components are provided as a dry powder, the powder can be reconstituted by the addition of a suitable solvent. It is envisioned that the solvent may also be provided in another container.

As indicated briefly above the kits may also contain a means by which to administer the antibody or the antigen-binding portion thereof and any optional components to a patient, e.g., one or more needles, I.V. bags or syringes, or even an eye dropper, pipette, or other such like apparatus, from which the formulation may be injected or introduced into the animal or applied to a diseased area of the body. The kits of the present disclosure will also typically include a means for containing the vials, or such like, and other component in close confinement for commercial sale, such as, e.g., injection or blow-molded plastic containers into which the desired vials and other apparatus are placed and retained.

The following abbreviations are used throughout the disclosure.

| Abbreviation | Full Name |
|---|---|
| CD47 | Cluster of differentiation 47 |
| SIRPα | Signal regulatory protein alpha |
| ECD | Extra-cellular domains |
| BMK | Benchmark |
| BMK1 | W345-BMK1.uIgG4PE.K or CC-90002 |
| BMK2 | W345-BMK2 or W345-BMK2.uIgG4.SP or Hu5F9-G4 |
| BMK4 | W345-BMK4.uIgG4.SPK or 2.3D11-IgG4 |
| BMK8 | W345-BMK8, 13H3 or TJ-C4 |
| PBMC | Peripheral Blood Mononuclear Cell |

-continued

| Abbreviation | Full Name |
|---|---|
| HA | Hemagglutination Activity |
| ADCC | Antibody-dependent cell-mediated cytotoxicity |
| CDC | Complement dependent cytotoxicity |
| DSF | Differential scanning fluorimetry |
| M-CSF | Macrophage Colony-Stimulating Factor |
| LDH | Lactate dehydrogenase |
| PBST | Phosphate buffered saline with 0.05% (v/v) Tween 20 |
| TMB | Tetramethylbenzidine |
| ELISA | Enzyme-linked immuno sorbent assay |
| FACS | Fluorescence-activated cell sorting |

Sequence Listing Summary

Appended to the instant application is a sequence listing comprising nucleic acid and amino acid sequences of the lead antibody W3455-4.9.9-uIgG4.SPL (also abbreviated as "W3455 antibody"). The following Tables A, B and C provide a summary of the included sequences.

TABLE A

CDR amino acid sequences

| | CDR1 | CDR2 | CDR3 |
|---|---|---|---|
| VH | SEQ ID NO: 1<br>GFTFSNFAMS | SEQ ID NO: 2<br>TISASGGRTFYADSVKG | SEQ ID NO: 3<br>EGSFGEGVDP |
| VL | SEQ ID NO: 4<br>SGDALPKKYAY | SEQ ID NO: 5<br>EDNKRPS | SEQ ID NO: 6<br>YSTDISGNHWV |

TABLE B

Variable region sequences

| VH<br>SEQ ID NO: 7 | VL<br>SEQ ID NO: 8 |
|---|---|
| EVQLLESGGGLVQPGGSLRL<br>SCAASGFTFSNFAMSWVRQ<br>APGKGLEWVSTISASGGRTF<br>YADSVKGRITISRDNSKNTL<br>FLQMNGLRAEDTAVYYCAK<br>EGSFGEGVDPWGQGTLVTV<br>SS | SYEMTQPPSVSVSPGQTARITCS<br>GDALPKKYAYWYQQKSGQAPVL<br>VIYEDNKRPSGIPERFSGSSSGT<br>MATLTISGAQVEDEADYYCYST<br>DISGNHWVFGGGTELTVL |
| VHnu<br>(heavy chain<br>variable<br>region<br>nucleotide<br>sequences)<br>SEQ ID NO: 9 | VLnu<br>(light chain<br>variable<br>region<br>nucleotide<br>sequences)<br>SEQ ID NO: 10 |
| GAAGTGCAGTTGTTGGAGT<br>CTGGGGGAGGCTTGGTACA<br>GCCTGGGGGGTCCCTGAGA<br>CTCTCCTGTGCAGCCTCTG<br>GATTCACCTTTAGCAACTT<br>TGCCATGAGCTGGGTCCGC<br>CAGGCTCCAGGGAAGGGG<br>CTGGAGTGGGTCTCAACTA<br>TTAGTGCTAGTGGTGGTCG<br>GACATTCTACGCAGACTCC<br>GTGAAGGGCCGGATCACCA<br>TCTCCAGAGACAATTCCAA<br>GAACACGCTGTTTCTGCAA<br>ATGAATGGCCTGAGAGCCG<br>AGGACACGGCCGTCTATTA<br>CTGTGCGAAGGAGGGGTCG<br>TTCGGGGAGGGAGTCGACC<br>CCTGGGGCCAGGGAACCCT<br>GGTCACCGTGTCCTCA | TCCTATGAGATGACACAGCCA<br>CCCTCGGTGTCAGTGTCCCCAG<br>GACAAACGGCCAGGATCACCT<br>GCTCTGGAGATGCATTGCCAA<br>AAAAATATGCTTATTGGTACCA<br>GCAGAAGTCAGGCCAGGCCCC<br>TGTGCTGGTCATCTATGAGGAC<br>AACAAACGACCCTCAGGGATC<br>CCTGAGAGATTCTCTGGCTCCA<br>GCTCAGGGACAATGGCCACCT<br>TGACTATCAGTGGGGCCCAGG<br>TGGAGGATGAAGCTGACTACT<br>ACTGTTACTCAACAGACATCAG<br>TGGTAATCATTGGGTGTTCGGC<br>GGAGGGACCGAGCTGACCGTC<br>CTA |

TABLE C

Full length sequences of heavy chain and light chain

| Heavy Chain SEQ ID NO: 11 | Light chain SEQ ID NO: 12 |
|---|---|
| EVQLLESGGGLVQPG | SYEMTQPPSVSVSPGQ |
| GSLRLSCAASGFTFS | TARITCSGDALPKKY |
| NFAMSWVRQAPGKGL | AYWYQQKSGQAPVLV |
| EWVSTISASGGRTFY | IYEDNKRPSGIPERF |
| ADSVKGRITISRDNS | SGSSSGTMATLTISG |
| KNTLFLQMNGLRAED | AQVEDEADYYCYSTD |
| TAVYYCAKEGSFGEG | ISGNHWVFGGGTELT |
| VDPWGQGTLVTVSSA | VLGQPKAAPSVTLFP |
| STKGPSVFPLAPCSR | PSSEELQANKATLVC |
| STSESTAALGCLVKD | LISDFYPGAVTVAWK |
| YFPEPVTVSWNSGAL | ADSSPVKAGVETTTP |
| TSGVHTFPAVLQSSG | SKQSNNKYAASSYLS |
| LYSLSSVVTVPSSSL | LTPEQWKSHRSYSCQ |
| GTKTYTCNVDHKPSN | VTHEGSTVEKTVAPT |
| TKVDKRVESKYGPPC | ECS |
| PPCPAPEFLGGPSVF | |
| LFPPKPKDTLMISRT | |
| PEVTCVVVDVSQEDP | |
| EVQFNWYVDGVEVHN | |
| AKTKPREEQFNSTYR | |
| VVSVLTVLHQDWLNG | |
| KEYKCKVSNKGLPSS | |

TABLE C-continued

Full length sequences of heavy chain and light chain

| Heavy Chain SEQ ID NO: 11 | Light chain SEQ ID NO: 12 |
|---|---|
| VFSCSVMHEALHNHY | |
| TQKSLSLSLGK | |

EXAMPLES

The present disclosure, thus generally described, will be understood more readily by reference to the following Examples, which are provided by way of illustration and are not intended to be limiting of the present disclosure. The Examples are not intended to represent that the experiments below are all or the only experiments performed.

Example 1

Preparation of Materials, Benchmark Antibodies and Cell Lines 1.1 Preparation of Materials Information on the commercially available materials and material codes used in the examples are provided in Tables 1 and 2, respectively.

TABLE 1

| Materials | Vendor | Cat. |
|---|---|---|
| Recombinant human CD47 Protein | Sino Biological | 12283-HCCH |
| Human SIRP alpha/CD172a Protein, mouse IgG1 Fc Tag (HPLC-verified) | Acribiosystem | SIA-H52A8 |
| Recombinant mouse SIRP alpha Protein (His Tag) | Sino Biological | 50956-M08H |
| Purified anti-mouse CD47 Antibody | Biolegend | 127501 |
| Recombinant Mouse IAP/OA3/CD47 (C-Fc) | Novoprotein | CM62 |
| Recombinant Human Thrombospondin-1 Protein, CF | R&D | 3074-TH |
| Recombinant human SIRP alpha Protein (His Tag) | Sino Biological | 11612-H08H |
| Tetramethylbenzidine (TMB) | Sigma | 860336-5G |
| R-PE goat anti-human IgG Fc | Jackson Immuno Research | 109-115-098 |
| Goat anti rat IgG-Fc-HRP | Bethly | A110-236P |
| Goat Anti-Rat IgG Fc Alexa647 | Jackson Immuno Research | 112-606-071 |
| Anti-His Tag Antibody [Biotin] | GenScript | A00613 |
| Streptavidin PE | eBioscience | 12-4317 |
| Goat anti-Human-IgG-Fc-HRP | Bethyl | A80-304P |
| Mouse anti-His Tag Antibody-HRP | GenScript | A00612 |
| CD14 Microbeads, Human | Miltenyi Biotec | 130-050-201 |
| Recombinant Human M-CSF Protein | R&D Systems | 216-MC/CF |
| CellTraceTM CFSE dye | Life Technologies | C34570 |
| APC Mouse Anti-Human CD14 | BD Pharmingen | 561708 |
| Cytotoxicity Detection Kit (LDH) | Roche | 04744 |
| Propidium Iodide (PI) Solution | Invitrogen | P3566 |
| Raji | ATCC | CCL-86 ™ |
| Jurkat.2B8 | ATCC (Subcloning in TAD) | TIB-152 ™ |
| CCRF-CEM | ATCC | CCL-119 ™ |
| A20 | ATCC | TIB-208 ™ |

TABLE C-continued

Full length sequences of heavy chain and light chain

| Heavy Chain SEQ ID NO: 11 | Light chain SEQ ID NO: 12 |
|---|---|
| IEKTISKAKGQPREP | |
| QVYTLPPSQEEMTKN | |
| QVSLTCLVKGFYPSD | |
| IAVEWESNGQPENNY | |
| KTTPPVLDSDGSFFL | |
| YSRLTVDKSRWQEGN | |

TABLE 2

| Materials Code | Materials Name/Information |
|---|---|
| W345-hPro1.ECD (sino) | Recombinant human CD47 Protein |
| WBP345-hPro1L1.ECD.mFc (Acrobio) | Human SIRP alpha/CD172a Protein, mouse IgG1 Fc Tag (HPLC-verified) |
| WBP345-mPro1L1.ECD.His (sino) | Recombinant mouse SIRP alpha Protein, (His Tag) |
| WBP345-cAb2 (Biolegend) | Purified anti-mouse CD47 Antibody |
| W345-mPro1.ECD.hFc (novoprotein) | Recombinant Mouse IAP/OA3/CD47 (C-Fc) |

TABLE 2-continued

| Materials Code | Materials Name/Information |
| --- | --- |
| W345-hPro1L2.His (R&D) | Recombinant Human Thrombospondin-1 Protein, CF |
| W345-hPro1L1.His (sino) | Recombinant human SIRP alpha Protein (His Tag) |
| BMK1 | CC-90002 from Celgene [6] |
| BMK2 | Hu5F9-G4 from Forty Seven Inc. [5], [7] |
| BMK4 | 2.3D11-IgG4 from Surface Oncology [8] |
| BMK8 | 13H3 or TJ-C4 from I-MAB [9] |

1.2 Production of Antigens

Human CD47 (NP_001768.1, NCBI) and cynomolgus monkey CD47 (XP_005548289.1, NCBI) extracellular domain (ECD) genes with Fc-tag were cloned into expression vector. Then, the plasmid was transfected into EXpi293 cells according to manufacturer's instructions (Expi293F Transfection Kit, Invitrogen). The cells were cultured in an incubator at 37° C., 8% $CO_2$ and then the supernatant was collected after 5 days of culturing. The antigen proteins were purified using Protein A column and SEC column.

1.3 Production of Benchmark Antibodies

DNA sequences encoding the variable regions of anti-CD47 antibodies BMK1, BMK2, BMK4 and BMK8 (see Table 2, as disclosed in references [5]-[9], which are incorporated herein in entirety by reference) were separately cloned into expression vectors with the constant region of human IgG4. Then, the plasmid was transfected into EXpi293 cells according to manufacturer's instructions (Expi293F Transfection Kit, Invitrogen). The cells were cultured in an incubator at 37° C., 8% $CO_2$ and then the supernatant was collected after 5 days of culturing. The proteins were purified using Protein A column and SEC column.

Benchmark antibodies, "W345-BMK1.uIgG4PE.K", "W345-BMK2. uIgG4.SP", "W345-BMK4.uIgG4.SPK" and W345-BMK8 were generated and applied as controls in the following examples. They were also referred to as W345-BMK1, W345-BMK2, W345-BMK4 and BMK8 herein, respectively.

1.4 Cell Pool/Line Generation

The full length gene of human (NP 001768.1, NCBI) or cynomolgus monkey CD47 (XP_005548289.1, NCBI) was cloned into an expression vector for development of cell lines. Briefly, the CHO—K1 cells at 70-90% confluents were transfected with human or monkey CD47 full length plasmid using lipofectamine 2000 reagent. The transfected cells were cultured in an incubator at 37° C., 5% CO2. 24 hours after transfection, blasticidin at a final concentration of 2-10 μg/mL was used to select the stable pool. Then, the positive pool cells were subcloned by limited dilution. Single clone was picked and tested by FACS using anti-CD47 antibodies.

Example 2

Antibody Hybridoma Generation 2.1 Animal Immunization and Serum Titer Detection

Four transgenic rats were purchased from Ligand and were housed in an IACUC approved animal facility. Human CD47 (NP_942088) or mouse CD47 (Q61735) extra-cellular domain (ECD) proteins and CD47 full length expression plasmids were used as immunogens for animal immunization with 30-100 μg/rat each time. Serum samples were collected from the animals before and after immunization and serum titers against target proteins were tested by ELISA according to general ELISA procedures.

The serum titer results were shown in Table 3. 1 #and 2 #rats with a much higher serum titer were chosen for electro-cell fusion.

TABLE 3

Serum titer summary

| | Animal serum titer against human CD47-ECD (ELISA) | | | |
| --- | --- | --- | --- | --- |
| | #1 | #2 | #3 | #4 |
| Pre-Titer | <100 | <100 | <100 | <100 |
| $1^{st}$ Titer | 72900 | 218700 | 24300 | 24300 |
| $2^{nd}$ Titer | 656100 | 1968300 | 72900 | 656100 |

2.2 Hybridoma Generation

The animals were sacrificed and B cells from spleens and lymph nodes were fused with SP2/0 myeloma cells by electro-fusion according to general electro-fusion procedures. After cell fusion, the cells were plated in 96-well plates with DMEM medium supplemented with 20% FBS and 1% HAT selective reagents. The plates were cultured in an incubator at 37° C., 5% $CO_2$ for 14 days with two medium changes on day 7 and day 10, and then followed by various screenings.

2.3 Hybridoma Screening and Subcloning

The hybridoma cells were screened by ELISA and FACS against human CD47 or cynomolgus monkey CD47 protein. The ability of CD47 antibodies to compete for SIRPα ligand binding to CD47 protein was assessed by FACS. Antibody-producing hybridoma cells were subcloned using semi-solid medium approach and subcloned hybridoma cells were re-screened using the methods as described above. After a series of screenings, positive clone WBP3455-4.9.9 was identified as the lead hybridoma clone and was further fully characterized.

2.4 Hybridoma Sequencing

The lead clone WBP3455-4.9.9 was identified and sequenced. RNA was extracted from the hybridoma cells and cDNA was amplified using 5'-RACE kit, followed by PCR amplification using 3'-degenerated primers and 3'-adaptor primers, and then PCR fragments were cloned into pMD18-T vector for sequencing.

The detailed variable domain amino acid sequences of WBP3455-4.9.9 were listed in Table 4.

TABLE 4

Variable domain amino acid sequence

| Clone ID | | FW1 | CDR1 | FW2 | CDR2 | FW3 | CDR3 | FW4 |
| --- | --- | --- | --- | --- | --- | --- | --- | --- |
| WBP3455-4.9.9 | VH | EVQL LESG GGLV QPGG SLRL SCAA S | GFTFSN FAMS | WVRQ APGK GLEW VS | TISA SGGR TFYA DSVK G | RITISEGSF RDNSKGEGV NTLFLDP QMNGL RAEDT AVYYC AK | | WGQGT LVTVS S |
| | VL | SYEM TQPP SVSV SPGQ TARI TC | SGDALP KKYAY | WYQQ KSGQ APVL VIY | EDNK RPS | GIPERYSTD FSGSSISGN SGTMAHWV TLTIS GAQVE DEADY YC | | FGGGT ELTVL |

Example 3

Generation of Lead Antibody W3455-4.9.9-uIgG4.SPL

Final lead antibody was constructed by converting variable regions of the heavy and light chains of original clone WBP3455-4.9.9 into human IgG4 backbone format with S228P mutation, and transfected into EXpi293 cells according to manufacturer's instructions (Expi293F Transfection Kit, Invitrogen). The supernatant of transient cells was collected and filtered, followed by a purification process using either Protein A column (GE Healthcare, 175438) or Protein G column (GE Healthcare, 170618).

The obtained antibody was named as "W3455-4.9.9-uIgG4.SPL" (same as "WBP3455-4.9.9-uIgG4.SPL" or "W3455-4.9.9-uIgG4L.SP"). The concentration of the purified antibody was determined by absorbance at 280 nm. The molecular weight and purity of the antibody were tested by SDS-PAGE and SEC-HPLC, respectively; and then stored at −80° C. until use.

The molecular weight and purification information of the lead antibody was summarized in Table 5. As can be seen, the purity of the lead antibody was above 95%.

TABLE 5

| mAb | PI | MW | Purity (% SEC-HPLC) | Yield (mg/L) | Endotoxin |
|---|---|---|---|---|---|
| W3455-4.9.9-uIgG4.SPL | 6.3 | 144 | 99.62 | 293 | <5 EU/mg |

Example 4

In Vitro Characterization of Lead Antibody W3455-4.9.9-uIgG4.SPL 4.1 Antibody Binding to Human CD47 Protein (ELISA)

Binding of the lead antibody to CD47 protein was determined by ELISA. The 96-well plates were coated with human CD47 ECD protein at 1 µg/mL at 4° C. overnight and blocked with 2% BSA-PBS for 1 hr. Then the lead antibody at various concentrations were added and incubated for 2 hr. Then the Goat anti-human IgG-Fc-HRP secondary antibody was added and incubated for 1 hr. The TMB peroxidase substrate solution was added and then reaction was stopped after 12 min using 2M HCl. All incubation steps were performed at room temperature, and the plates were washed 5 times with PBST at pH 7.4 between steps. The absorbance of testing samples is measured at 450 nm with a multiwall plate reader (SpectraMax® M5e). The binding EC50s were analyzed by using GraphPad Prism software equation: Nonlinear regression (curve fit)—log (agonist) vs. response—Variable slope.

As shown in FIG. 1, the result indicated that the lead mAb could bind to human CD47 ECD protein with high affinity. The binding $EC_{50}$ and Max OD were comparable among the lead mAb and the three benchmark controls.

4.2 Antibody Binding to Human or Cynomolgus Monkey CD47-Expressing Cells (FACS)

Binding of lead antibody to human CD47 or cyno CD47 expressing cells was determined by FACS. Briefly, the engineered CD47-expressing cells were coated into 96-well U-bottom plates at a density of 1×10$^5$ cells/well and centrifuged at 1500 rpm at 4° C. for 4 min before removing the supernatant. Then the lead antibody at various concentrations were added to re-suspend cells and incubated at 4° C. for 1 hr. The cells were washed twice with 180 µL 1% BSA-PBS. The secondary antibody, Goat Anti-human IgG-Fc PE was added to re-suspend cells and incubated at 4° C. in the dark for 30 min followed by washing with 180 µL 1% BSA-PBS. At the end, the cells were re-suspended in 100 µL 1% BSA-PBS, and the fluorescence intensity was measured by FACS (BD Canto II) and analyzed by FlowJo Version software. The binding EC50s were calculated by using GraphPad Prism software equation: Nonlinear regression (curve fit)—log (agonist) vs. response—Variable slope.

Figure 2:
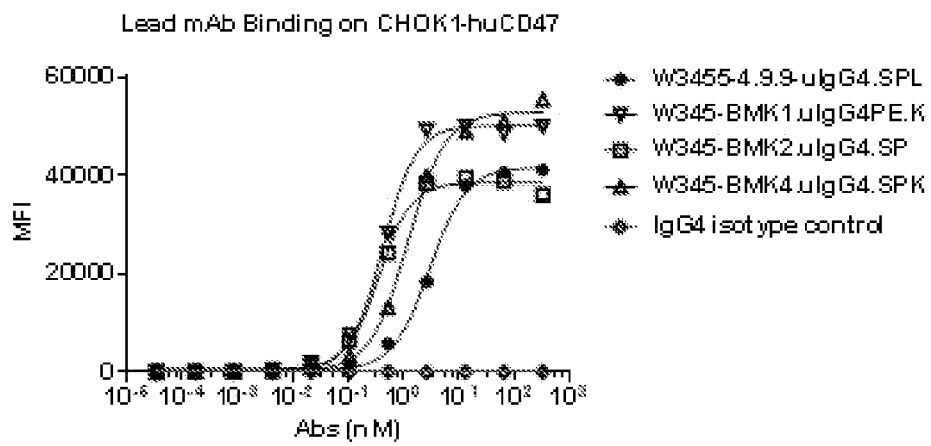
FIG. 2 shows the binding of lead antibody W3455 to human CD47-expressing cells, as measured by FACS. The "Neg" column is the max MFI of a blank control.
Figure 3:
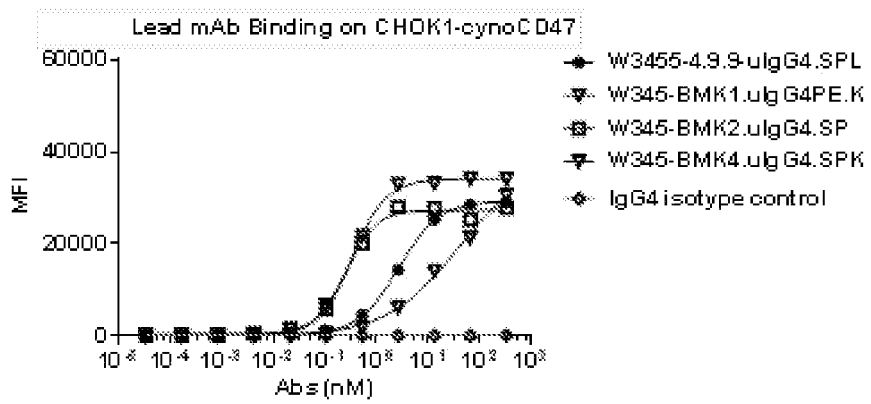
FIG. 3 shows the binding of lead antibody W3455 to cynomolgus monkey CD47-expressing cells, as measured by FACS.

As shown in FIGS. 2 and 3, the result indicated that the lead mAb could bind to human CD47-expressing cells and cyno CD47 expressing cells with a high and comparable affinity.

4.3 Antibody Binding to Human RBC (FACS)

Since CD47 was expressed on human red blood cells (RBCs), the binding activity of W3455-4.9.9-uIgG4.SPL on human RBCs was evaluated by FACS. Human red blood cells were isolated from trisodium citrate-treated fresh human blood by centrifuging at 2000 rpm for 10 min and discarding the supernatant serum. Human RBC cells were coated into 96-well U-bottom plates at a density of 1×10$^5$ cells/well and centrifuged at 1500 rpm at 4° C. for 4 min before removing the supernatant. Then the lead antibody at various concentrations were added to re-suspend cells and incubated at 4° C. for 1 hr. The cells were washed twice with 180 µL 1% BSA-PBS. The secondary antibody, Goat Anti-human IgG-Fc PE was added to re-suspend cells and incubated at 4° C. in the dark for 30 min followed by washing with 180 µL 1% BSA-PBS. At the end, the cells were re-suspended in 100 µL 1% BSA-PBS, and the fluorescence intensity was measured by FACS (BD Canto II) and analyzed by FlowJo Version software. The binding EC50s were calculated by using GraphPad Prism software equation: Nonlinear regression (curve fit)—log (agonist) vs. response—Variable slope.

Figure 4:
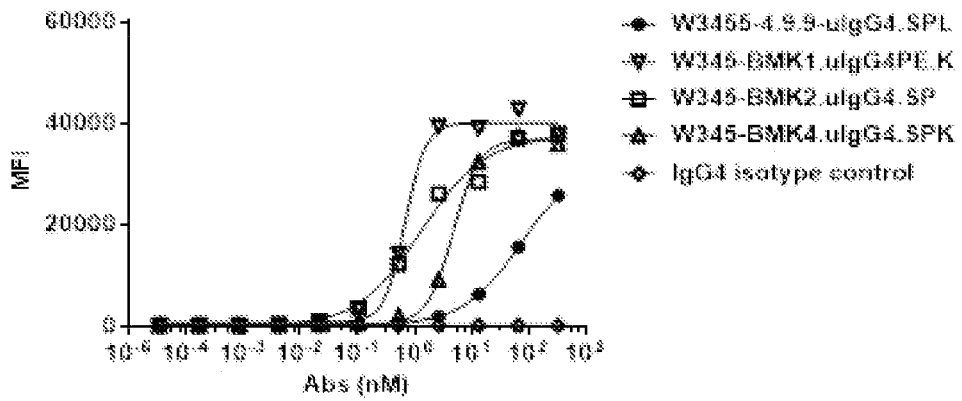
FIG. 4 shows the binding of lead antibody W3455 to human red blood cells, as measured by FACS.

As shown in FIG. 4, the result indicated that the lead mAb could bind to human RBCs with much lower affinity compared to benchmark antibodies, which may have significant benefits in improving anemia in clinical trials.

4.4 Human RBC hemagglutination assay (HA)

To evaluate hemagglutination activity (HA) of W3455-4.9.9-uIgG4.SPL on RBCs, HA was performed using human red blood cells (hRBC). Human RBCs were isolated from trisodium citrate-treated fresh human blood by centrifuging at 2000 rpm for 10 min and discarding the supernatant serum. 25 uL of hRBC suspension diluted with DPBS were added to U-bottom 96-well plate (approximately ~4×10$^6$ RBC/well), followed by addition of 25 uL of lead antibodies (dilution range from 667 nM to 0.667 nM, equal to 100 ug/ml to 0.1 ug/ml), then mixed well gently and incubated at 37° C. for 1 hr. The RBC were re-suspended in DPBS and examined under microscope.

Figure 5:
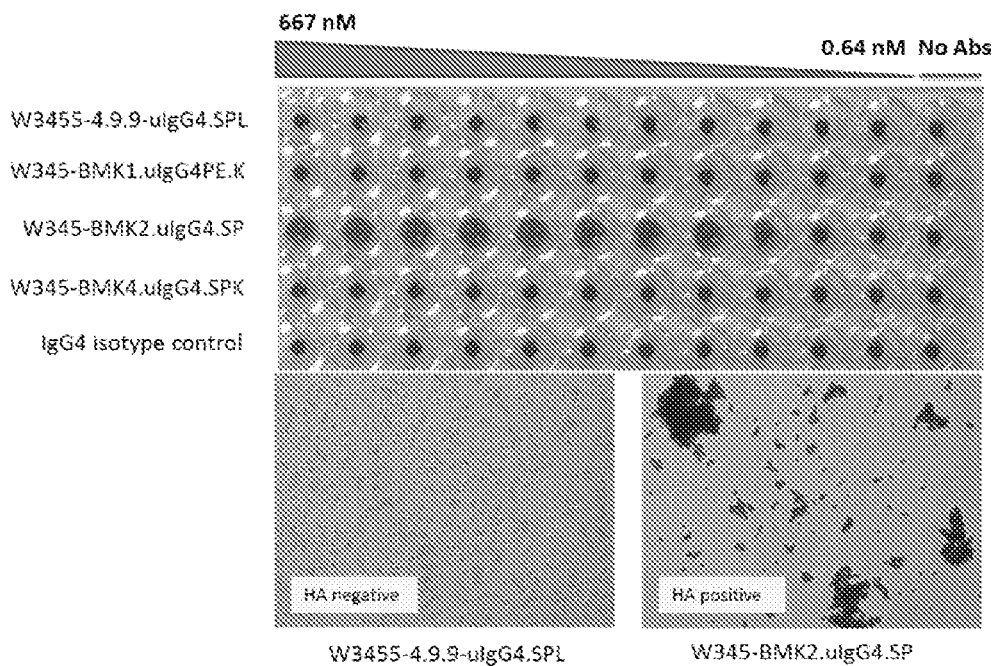
FIG. 5 shows the hemagglutination activity (HA) of lead antibody W3455 on human RBCs.

The formation of RBC clusters was defined as HA positive as shown in FIG. 5 (W345-BMK2), whereas RBCs remaining in intact and dissociative condition were defined as HA negative (isotype control). As shown in FIG. 5, the result indicated that the RBCs added with the lead mAb remained in intact and dissociative condition without any RBC cluster formation and were therefore defined as HA negative, whereas W345-BMK2.uIgG4.SP induced significant RBC clusters indicating hemagglutination positive.

4.5 Human Ligand Competition Assay (ELISA)

To assess ligand (SIRPα) blocking activity of W3455-4.9.9-uIgG4.SPL, the protein-based competition assay was performed by ELISA. 96-well plates were coated with human CD47 ECD at 1 µg/mL at 4° C. overnight and blocked with 2% BSA-PBS for 1 hr. The mixture of lead antibody at various concentrations and human SIRPα (1 ug/ml) was added and incubated for 2 hr. The secondary antibody mouse anti-His tag-HRP was added and incubated for 1 hr. The TMB peroxidase substrate solution was added and then reaction was stopped after 12 minutes using 2M HCl. All incubation steps were performed at room temperature, and the plates were washed with PBST between steps. The absorbance of the testing samples was measured at 450 nm with a multiwall plate reader. The competitive binding IC50s were calculated by using GraphPad Prism software equation: Nonlinear regression (curve fit)—log (antagonist) vs. response—Variable slope.

Figure 6:
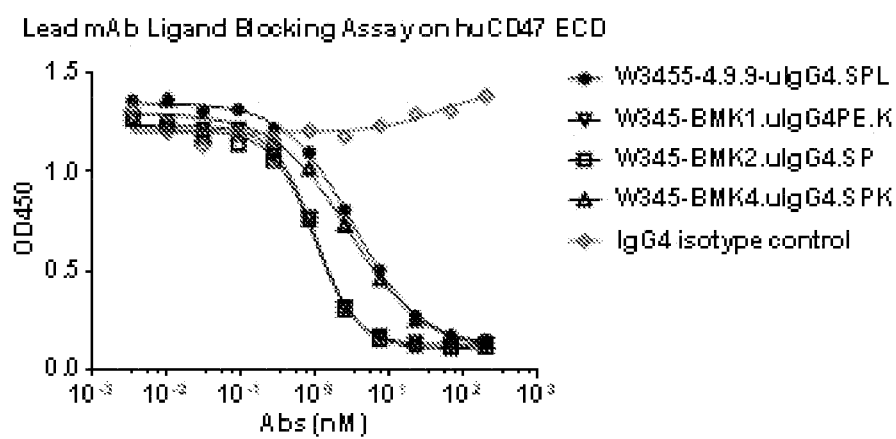
FIG. 6 shows SIRPα blocking activity of lead antibody W3455 determined by ELISA in a ligand competition assay. The "Min OD" refers to the minimal OD450 value, and the "Ligand" column refers to the Min OD result when only the ligand is present.

As shown in FIG. 6, the data indicated that the lead mAb could competitively block the binding interaction between CD47 and SIRPα (ligand) with an inhibitory rate >85%. The inhibition rate was calculated using the equation: [(OD450$_{ligand\ only}$−OD450$_{blocking\ samples}$)/OD450$_{ligand\ only}$× 100%].

4.6 Human Ligand Competition Assay (FACS)

To assess ligand (SIRPα) blocking activity of W3455-4.9.9-uIgG4.SPL, the cell-based competition assay was performed using human CD47-expressing stable cells. Briefly, the engineered cells expressing human CD47 were coated onto 96-well U-bottom plates with 1×10$^5$ cells/well and centrifuged at 1500 rpm at 4° C. for 4 min before removing the supernatant. The mixture of lead mAbs at various concentrations and human SIRPα protein (1 ug/ml) was added and incubated for 2 hr. The cells were washed twice with 200 μL 1% BSA-PBS. The secondary antibody, mouse anti-His tag-Biotin was added to re-suspend cells and incubated at 4° C. in the dark for 1 h followed by washing with 200 μL 1% BSA-PBS. The third antibody, anti-Streptavidin-PE was added to re-suspend cells and incubated at 4° C. in the dark for 30 min followed by washing with 200 μL 1% BSA-PBS. At the end, the cells were re-suspended in 100 μL 1% BSA-PBS, and the fluorescence intensity was measured by FACS (BD Canto II) and analyzed by FlowJo Version software. The competitive binding IC50s were calculated by using GraphPad Prism software equation: Nonlinear regression (curve fit)—log (antagonist) vs. response—Variable slope.

Figure 7:
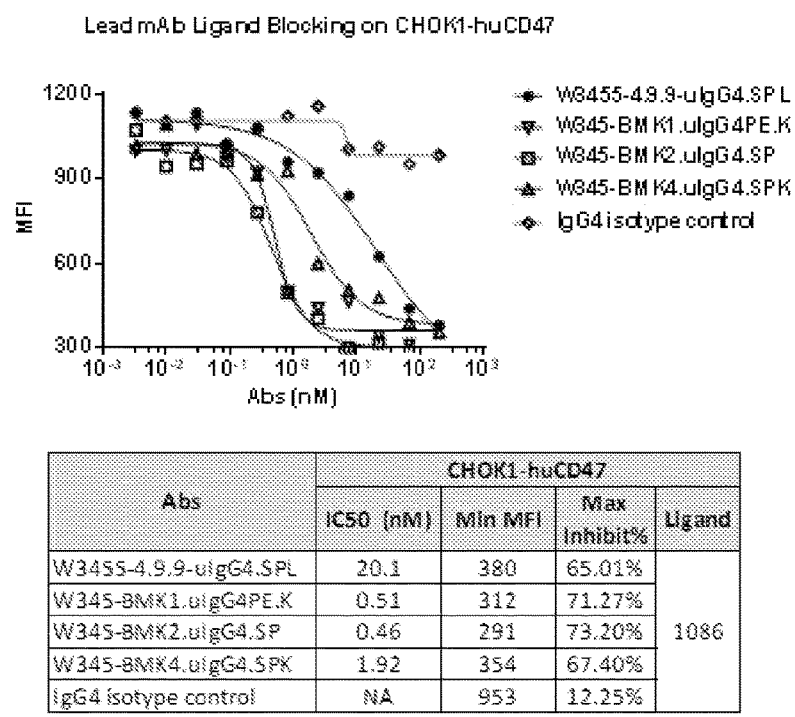
FIG. 7 shows SIRPα blocking activity of lead antibody W3455 determined by FACS in a ligand competition assay. The "Min MFI" refers to the minimal MFI value, and the "Ligand" column refers to the Min MFI result when only the ligand is present.

As shown in FIG. 7, the result indicated that the lead mAb could competitively block the binding of human CD47 to its ligand SIRPα.

4.7 Human CD47 Affinity (SPR)

Human CD47 binding affinity of W3455-4.9.9-uIgG4.SPL was performed by SPR assay using Biacore T200. Each antibody was captured on an anti-human IgG Fc antibody immobilized CM5 sensor chip (GE). Human CD47 protein at different concentrations were injected over the sensor chip at a flow rate of 30 uL/min for an association phase of 180 s, followed by 3600 s dissociation. The chip was regenerated by 10 mM glycine (pH 1.5) after each binding cycle. The sensorgrams of blank surface and buffer channel were subtracted from the test sensorgrams. The experimental data was fitted by 1:1 model using Langmiur analysis. Molecular weight of 55 kDa was used to calculate the molar concentration of analyte antigen.

Figure 8:
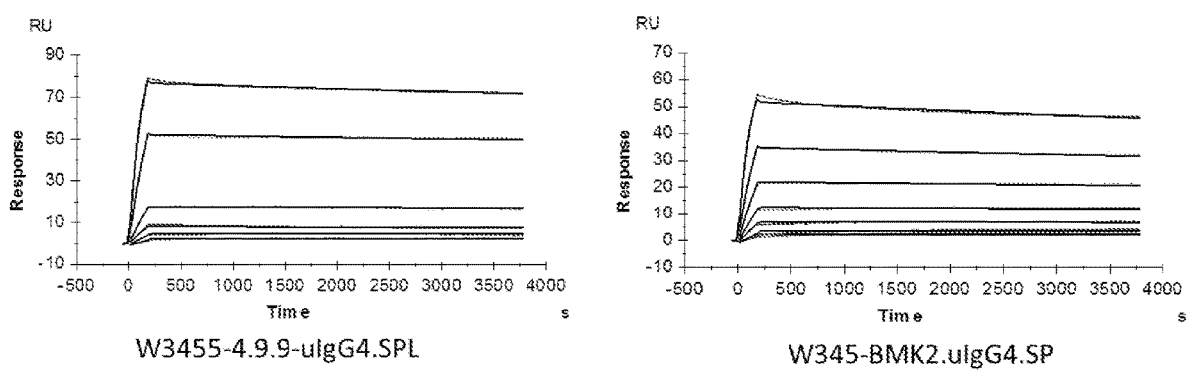
FIG. 8 shows the binding kinetics curves of lead antibody W3455 and benchmark antibody W345-BMK2.uIgG4.SP to human CD47, as measured by SPR.

The affinity KD value was shown in Table 6 and the binding kinetics curve were shown in FIG. 8. Both indicated that the lead mAb could bind to human CD47 with a high affinity, slightly better than the benchmark antibody W345-BMK2.uIgG4.SP.

TABLE 6

Lead mAb human CD47 binding affinity data by SPR

| Antigen | Antibody | ka (1/Ms) | kd (1/s) | KD (M) |
|---|---|---|---|---|
| Human CD47 ECD | W3455-4.9.9-uIgG4.SPL | 1.05E+06 | 2.34E−05 | 2.23E−11 |
| | W345-BMK2.uIgG4.SP | 9.69E+05 | 4.02E−05 | 4.14E−11 |

4.8 Thermal Stability

Differential scanning fluorometry (DSF) was used to evaluate lead mAb thermal stability. Briefly, the T$_m$ of antibodies was investigated using QuantStudio™ 7 Flex Real-Time PCR system (Applied Biosystems). 19 μL of antibody solution was mixed with 1 μL of 62.5×SYPRO Orange solution (Invitrogen) and transferred to a 96 well plate (Biosystems). The plate was heated from 26° C. to 95° C. at a rate of 0.9° C./min, and the resulting fluorescence data was collected. The negative derivatives of the fluorescence changes with respect to different temperatures were calculated, and the maximal value was defined as melting temperature T$_m$. If a protein has multiple unfolding transitions, the first two T$_m$ were reported, named as T$_m$1 and T$_m$2. Data collection and T$_m$ calculation were conducted automatically by the operation software.

Figure 9:
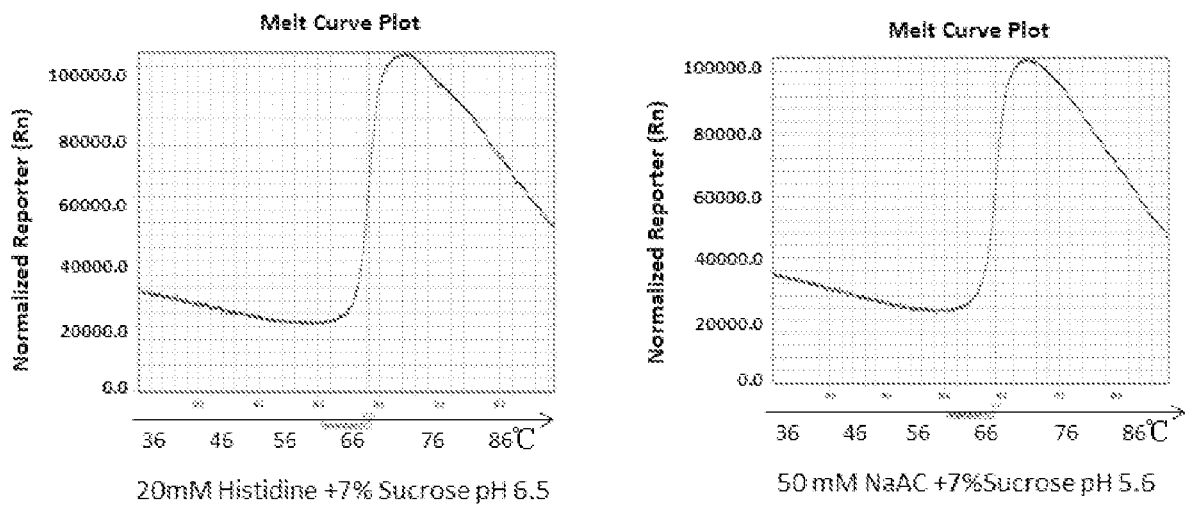
FIG. 9 shows thermal stability result of lead antibody W3455 in two different buffers, as measured by Differential scanning fluorometry (DSF).

As shown in FIG. 9 and Table 7 below, the result indicated that the lead mAb displayed good thermal stability in two different buffers.

TABLE 7

Lead mAb thermal stability testing by DSF

| mAb | PI | Buffer | Tm1 (° C.) | Tm2 (° C.) | T$_m$ Traffic Light |
|---|---|---|---|---|---|
| W3455-4.9.9-uIgG4.SPL | 6.3 | 20 mM Histidine + 7% Sucrose pH 6.5 | 64.4 | — | Pass |
| | 6.3 | 50 mM NaAC + 7% Sucrose pH 5.6 | 64.9 | — | |

4.9 Serum Stability

Serum stability assay of the lead mAb was performed in human serum. Freshly collected human blood was statically incubated in polystyrene tubes without anticoagulant for 30 min at room temperature. Serum was collected after centrifugation the blood at 4000 rpm for 10 min. Gently mixing antibodies with serum and the serum-antibody mixture was incubated at 37° C. The samples were collected on 0 day, 1 day, 4 days, 7 days and 14 days, respectively and were quickly-frozen down at the indicated time at −80° C. until use. The samples were used to assess their binding ability to human CD47-expression cells. Briefly, serial dilutions of antibodies were added to CD47 expression cells and incubated for 1 hr at 4° C. The cells were washed two times with 200 μL PBS with 1% BSA. PE conjugated goat anti-human IgG Fc diluted 1:150 with FACS buffer were added to the cells and incubated at 4° C. for 30 minutes. Additional washing steps were performed two times with 200 μL FACS buffer followed by centrifugation at 1500 rpm for 4 min at 4° C. Finally, the cells were re-suspended in 100 μl FACS buffer and fluorescence values were measured by FACS and analyzed by FlowJo.

Figure 10:
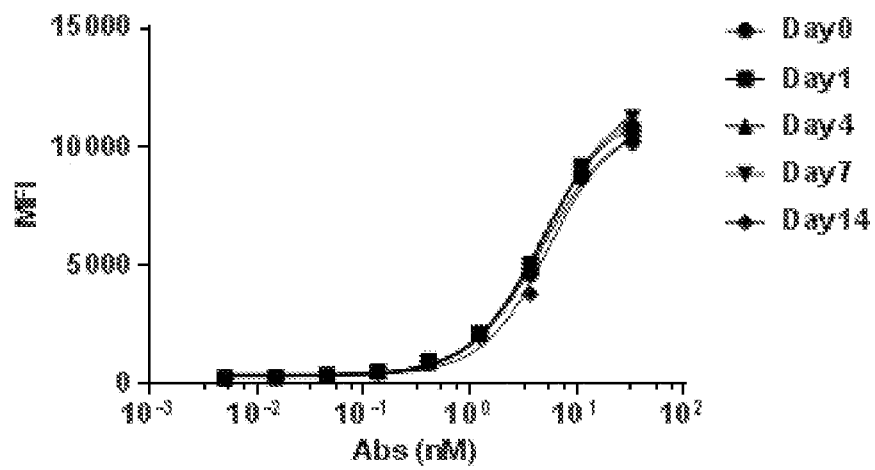
FIG. 10 shows the stability of lead antibody W3455 in human serum, as tested by FACS.

As shown in FIG. 10, the result indicated that serum culturing has no effect on the binding ability of lead mAb to human CD47. The binding of lead mAb did not change over time, as the lead mAb was stable in 37° C. human serum for at least 14 days.

4.10 Non-Specific Protein Binding (ELISA)

The non-specific binding of the lead mAb against 14 different proteins was tested by ELISA. The 96-well high binding plates were coated with 14 different proteins at 1 μg/mL at 4° C. overnight and blocked with 2% BSA-PBS for 1 hr. The lead antibody at 10 ug/ml was added and incubated for 2 hrs. Then the Goat anti-human IgG-Fc-HRP secondary antibody was added and incubated for 1 hr. The TMB peroxidase substrate solution was added and then reaction was stopped after 12 minutes using 2M HCl. All incubation steps were performed at room temperature, and the plates were washed 5 times with PBST at pH 7.4 between steps. The absorbance of testing samples was measured at 450 nm with a multiwall plate reader (SpectraMax® M5e).

The OD450 values were summarized in Table 8 below. The data indicated that the lead antibody showed no non-specific binding to 14 tested proteins.

TABLE 8

Lead mAb non-specific binding assay by ELISA

| mAbs | ELISA-OD450 | | | | | | | |
|---|---|---|---|---|---|---|---|---|
|  | Factor Eight | FGFR.his | CD147.his | PD-1.his | CTLA4.his | VEGFR2.his | CD22.his | VEGF.his |
| W3455-4.9.9-uIgG4L.SP | 0.0498 | 0.1381 | 0.0463 | 0.2269 | 0.0573 | 0.0452 | 0.0478 | 0.0475 |
| hIgG4K Isotype control | 0.1813 | 0.1326 | 0.0424 | 3.707 | 0.0562 | 0.0432 | 0.0451 | 0.0452 |
| hIgG4L Isotype control | 0.0481 | 0.1373 | 0.0443 | 0.2273 | 0.0571 | 0.0441 | 0.0467 | 0.0463 |

| mAbs | ELISA-OD450 | | | | | | |
|---|---|---|---|---|---|---|---|
|  | CD3.his | HER3.his | OX40.his | 4-1B8.his | CD40.his | HSA. | Background |
| W3455-4.9.9-uIgG4L.SP | 0.0527 | 0.0462 | 0.0487 | 0.0551 | 0.2091 | 0.3241 | 0.074 |
| hIgG4K Isotype control | 0.0479 | 0.044 | 0.0508 | 0.0463 | 0.2129 | 0.3218 | 0.0697 |
| hIgG4L Isotype control | 0.0518 | 0.0445 | 0.051 | 0.0463 | 0.2048 | 0.3349 | 0.0702 |

4.11 Non-Specific Cell Binding (FACS)

The non-specific binding of the lead mAb against 14 different human origin tumor cells and rat-derived CHO—K1 cells was conducted by FACS. The 14 different cells were transferred into 96-well U-bottom plates with 1×10⁵ cells/well and centrifuged at 1500 rpm for 4 min at 4° C. before removing supernatant. The lead antibody at 10 μg/ml was added to the cells and incubated at 4° C. for 1 hr. The cells were washed twice with 180 μL 1% BSA-PBS. Goat Anti-Human IgG Fc PE secondary antibody (Jackson, Catalog number 109-115-098) was added to re-suspend cells and incubated at 4° C. in the dark for 30 min. Additional washing steps were performed twice with 180 μL 1% BSA/1×PBS followed by centrifugation at 1500 rpm for 4 min at 4° C. Finally, the cells were re-suspended in 100 μL 1% BSA-PBS, and then fluorescence intensity was measured by flow cytometry (BD Canto II) and analyzed by FlowJo.

The MFI values were summarized in the table below. The data indicated that lead mAb could bind to all 14 human origin tumor cells tested, but did not bind with hamster origin CHO—K1 cell, indicating CD47 is widely expressed on human tumor cells.

TABLE 9

Lead mAb non-specific binding assay by FACS

| mAbs | FACS-MR | | | | | | |
|---|---|---|---|---|---|---|---|
|  | Ramos | MDA-MB-453 | BT474 | Jurkat.268 | Hut78 | A431 | A204 | CaLu-6 |
| W3455-4.9.9-uIgG4L.SP | 2328 | 584 | 1317 | 12600 | 3064 | 4372 | 3115 | 1807 |
| hIgG4K Isotype control | 74.4 | 32.2 | 20.8 | 36.9 | 49.7 | 39.5 | 34.7 | 23.3 |
| hIgG4L Isotype control | 68.4 | 28.3 | 19.1 | 64.3 | 50.2 | 251 | 42.4 | 88.4 |

| mAbs | FACS-MR | | | | | | |
|---|---|---|---|---|---|---|---|
|  | A375 | HepG2 | BxPC-3 | HT29 | FaOb | 293F | CHO-K1 |
| W3455-4.9.9-uIgG4L.SP | 1356 | 222 | 2061 | 2390 | 5754 | 2617 | 31.5 |
| hIgG4K Isotype control | 22.8 | 32.2 | 42.9 | 44.3 | 36.2 | 56.4 | 30.7 |
| hIgG4L Isotype control | 49.5 | 27.3 | 110 | 45.7 | 429 | 28.7 | 29.9 |

4.12 Phagocytosis Assay (FACS)

Phagocytic activity of lead mAb was evaluated using human PBMC-derived macrophages and two tumor cell lines of Jurkat cells, Raji cells, and human RBC as target cells.

Human PBMCs were isolated from fresh human blood, and the CD14 positive monocytes were isolated from PBMC by hCD14 Microbeads. The CD14 positive monocytes were differentiated into macrophages by incubating them in the 10% FBS RPIM1640 medium with 100 ng/ml rhM-CSF for 7 days. These monocyte derived macrophages (MDMs) became adherent allowing other cells to be washed away. MDMs were scraped and seeded into 96 well plates. Several human tumor cell lines or human RBCs were chosen as a target cell type because of their high CD47 expression. Target cells were labeled with 1 uM CFSE at 37° C. for 30 min, then washed and added to MDMs at a ratio of 1:1 tumor cells per phagocyte, and CD47 antibody was added at various concentrations. Phagocytosis of target cells was allowed for 2 hours, then stained with an antibody to the macrophage marker CD14 conjugated to APC, and analyzed by flow cytometry. Phagocytosis was measured by gating on live cells that were FL4 positive (CD14+), and then assessing the percent of FL1 (CFSE+) positive cells.

The macrophages that ingested tumor cells were counted and calculated as an index: Phagocytosis Index %=Percentage$_{CFSE+/CD14-APC+}$/(Percentage$_{CFSE+/CD14-APC+}$+Percentage$_{CFSE-/CD14-APC+}$)×100%.

Figure 11:
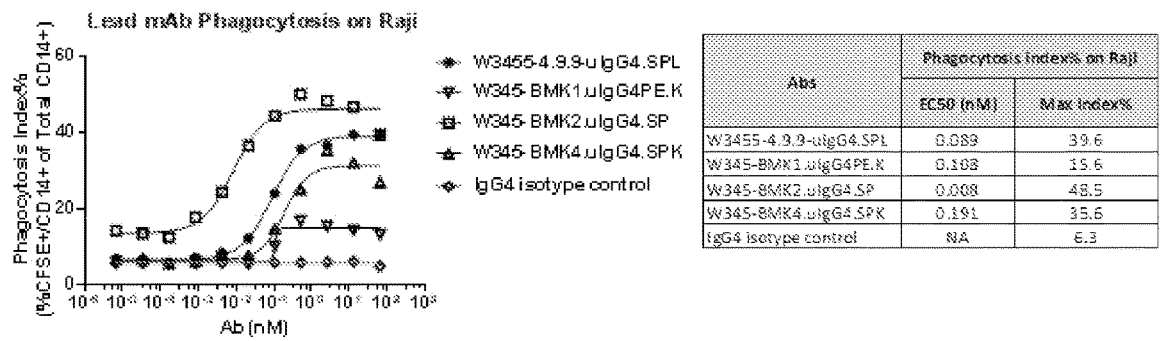
FIGS. 11A-11C show macrophage-mediated phagocytosis induced by lead antibody W3455 in Raji cells (A), Jurkat cells (B), and human RBCs (C).
Figure 11:
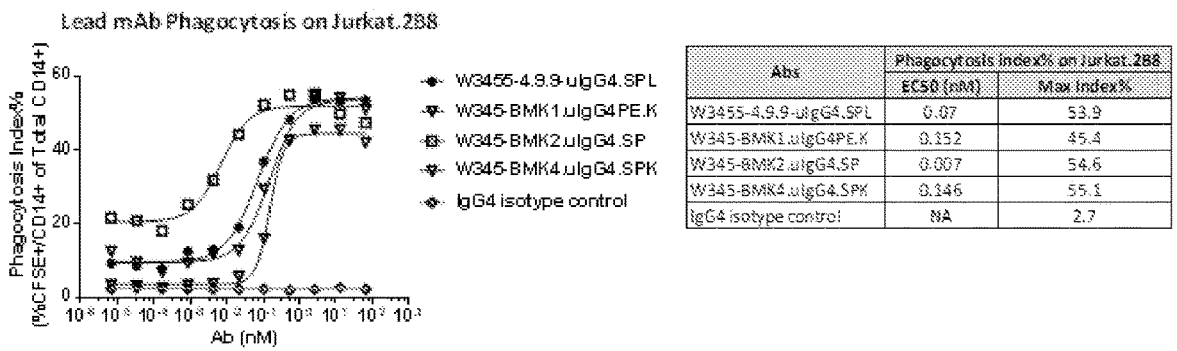
Figure 11:
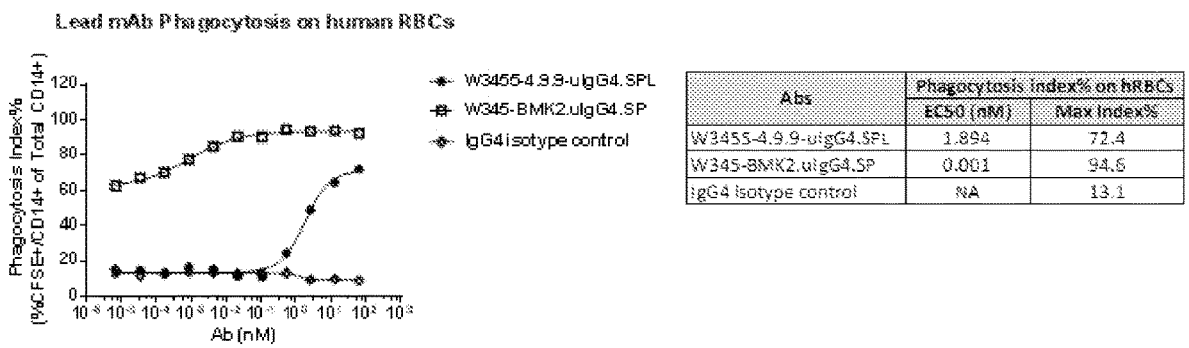

As shown in FIG. 11, lead mAb induced potent phagocytosis of tumor cells, comparable to benchmark antibodies and slight better than W345-BMK1.uIgG4PE.K and W345-BMK4.uIgG4.SPK (FIG. 11A-B). Surprisingly, the phagocytosis against human red blood cells for lead mAb was relatively low than W345-BMK2.uIgG4.SP (FIG. 11C).

4.13 ADCC Assay and CDC Assay

The lead mAb was evaluated for its ADCC and CDC activity on CCRF-CEM and Raji cells. PBMCs were used as effector cells and CCRF-CEM or Raji were used as target cells.

ADCC assay: Human PBMCs were isolated from fresh human blood. 2×10$^4$ target cells in 40 μL RPMI1640 (no phenol) medium containing 1% FBS were added per well in a 96-well U-bottom plate. Then, serial-diluted antibodies in 20 μL RPMI1640 (no phenol) medium containing 1% FBS were added to each well. After 15 min incubation at 37° C., 4×10$^5$ PBMCs in 40 μL RPMI1640 (no phenol) medium containing 1% FBS were added to each well to give a 20:1 E/T ratio. After incubation at 37° C. for 4 hr, mixtures were centrifuged at 1500 rpm for 5 min and 70 μL of supernatant was transferred for detection. Cell death was evaluated using LDH Cytotoxicity Detection Kit (Roche) according to manufacturer's instructions.

CDC assay: 2×10$^4$ target cells in 40 μL RPMI1640 (no phenol) medium containing 1% FBS were added per well in a 96-well U-bottom plate. Then, serial-diluted antibodies in 20 μL RPMI1640 (no phenol) medium containing 1% FBS were added to each well. After 15 min incubation at 37° C., normal human complement in 40 μL RPMI1640 (no phenol) medium containing 1% FBS were added to each well. After incubation at 37° C. for 4 hr, mixtures were centrifuged at 1500 rpm for 5 min and 70 μL of supernatant was transferred for detection. Cell death was evaluated using LDH Cytotoxicity Detection Kit (Roche) according to manufacturer's instructions.

Figure 12:
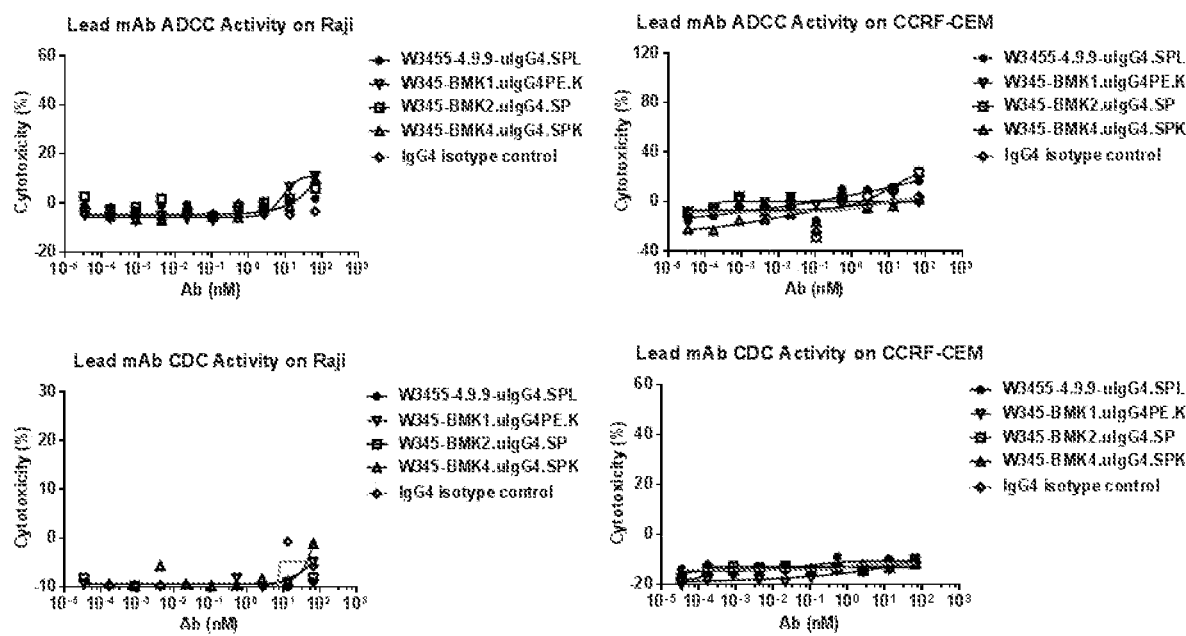
FIG. 12 shows the ADCC and CDC activity of lead antibody W3455 and benchmark antibodies on CCRF-CEM and Raji cells.

As shown in FIG. 12, the result indicated that the lead mAb and other benchmark antibodies induced weak or no ADCC and CDC activity both on CCRF-CEM and Raji tumor cells.

Example 5

In Vivo Characterization of Lead Antibody W3455-4.9.9-uIgG4.SPL 5.1 Anti-Tumor Efficacy in B-NDG Mice Model (Raji Cells)

Lead mAb efficacy study was conducted using Raji-Luc lymphatic cancer model in B-NDG mice by Biocytogen Co, Ltd. The cells were cultured in RPMI1640 medium supplemented with 10% heat inactivated fetal bovine serum at 37° C. in an atmosphere of 5% CO2 in air. The tumor cells were routinely sub-cultured twice a week with 0.25% trypsin-EDTA treatment. The cells growing in an exponential growth phase were harvested and counted for tumor inoculation.

For the therapeutic model, each mouse was inoculated intravenously with Raji-Luc lymphatic cancer cells (5.0× 10$^5$). Tumor growth was monitored as live imaging values twice per week by animal live imager. When the live imaging signal value of tumor reached approximately 1.05× 10$^6$ p/sec/cm$^2$/sr, animals were randomly grouped into five groups, and were studied with two dose levels at 3 mg/kg and 0.5 mg/kg. The animal study design was shown in table 10. The day of grouping was considered as day 0 and the mice were injected intraperitoneally twice per week for a total of 6 times at day 0, day 4, day 7, day 11, day 14 and day 18 post grouping, respectively. For all tumor-bearing mice, the live imaging values of tumor and body weight of mice were measured twice per week. All the procedures related to animal handling, care and the treatment in the study were performed according to the guidelines approved by the Institutional Animal Care and Use Committee (IACUC) of Shanghai Bio-model following the guidance of the Association for Assessment and Accreditation of Laboratory Animal Care (AAALAC).

TABLE 10

Anti-tumor efficacy study plan

| Group No. | Drug name | Dose level (mg/kg) | Dosing strategy | Dosing Route |
|---|---|---|---|---|
| G1 | IgG4 isotype control | 3 | Twice a week | Intraperitoneal injection |
| G2 | W3455-4.9.9-uIgG4L.SP | 3 | | |
| G3 | W3455-4.9.9-uIgG4L.SP | 0.5 | | |
| G4 | W345-BMK2.uIgG4.SP | 3 | | |
| G5 | W345-BMK2.uIgG4.SP | 0.5 | | |

Tumor growth was monitored as live luminescence signal intensity (imaging values expressed in p/sec/cm$^2$/sr) twice or thrice weekly by animal live imager. The results were represented by mean and the standard error (Mean±SEM). Data was analyzed using Two way ANOVA Bonferroni post-tests with Prism and P<0.05 was considered to be statistically significant.

Figure 13:
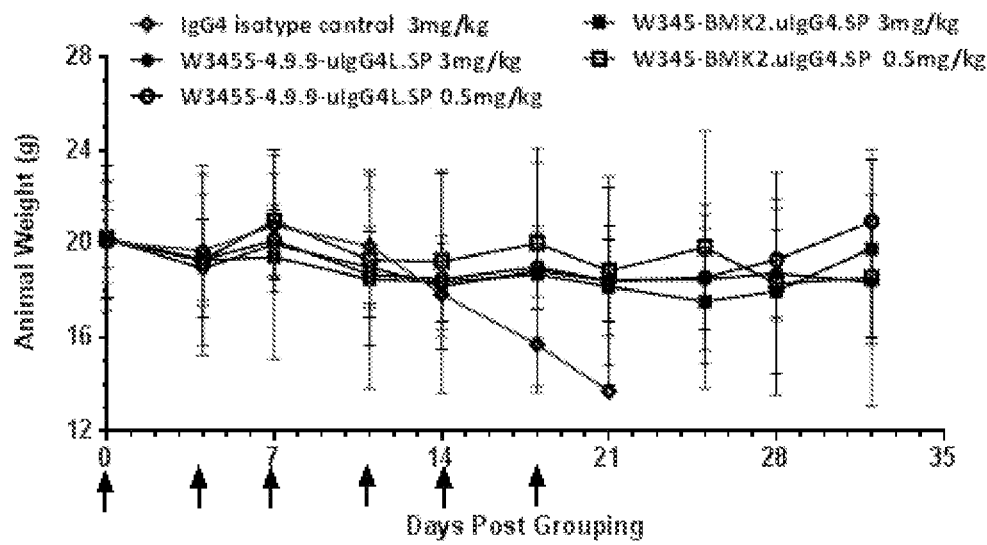
FIG. 13 shows the body weight changes of B-NDG mice inoculated with Raji-Luc lymphatic cancer cells after treatment of lead antibody W3455 or benchmark antibodies at different concentrations.

As shown in FIG. 13 and Table 11, at day 18 post grouping, compared with G1 (IgG4 isotype control, 3 mg/kg) vehicle group, mean body weight of the animals in G2 group to G5 group showed no significant reduction, which indicated W3455-4.9.9-uIgG4L.SP and W345-BMK2.uIgG4.SP were not toxic. The black arrow in FIG. 13 indicated the dosing time. Data was expressed as Mean±SEM, n=7.

TABLE 11

Body weight before grouping and day 18 post grouping

| Groups | Test articles | Body weight (g)[a] before grouping | Body weight (g)[a] day 18 post grouping | P value[b] | Body weight change (g) |
|---|---|---|---|---|---|
| G1 | IgG4 isotype control 3 mg/kg | 20.1 ± 0.7 | 15.7 ± 1.0 | — | −4.4 |
| G2 | WBP3455-4.9.9-uIgG4L.SP 3 mg/kg | 20.2 ± 0.9 | 18.9 ± 0.6 | 0.020 | −2.3 |
| G3 | WBP3455-4.9.9-uIgG4L.SP 0.5 mg/kg | 20.2 ± 0.5 | 19.0 ± 0.7 | 0.020 | −1.2 |
| G4 | W345-BMK2.uIgG4.SP 3 mg/kg | 20.1 ± 0.9 | 18.7 ± 1.8 | 0.271 | −1.4 |
| G5 | W345-BMK2.uIgG4.SP 0.5 mg/kg | 20.3 ± 1.2 | 20.0 ± 1.5 | 0.081 | −0.2 |

Notes:
[a] Mean ± SEM.
[b] Statistical analysis of mean body weight at day 18 post grouping using T-test between G1 group and the treatment group.

Figure 14:
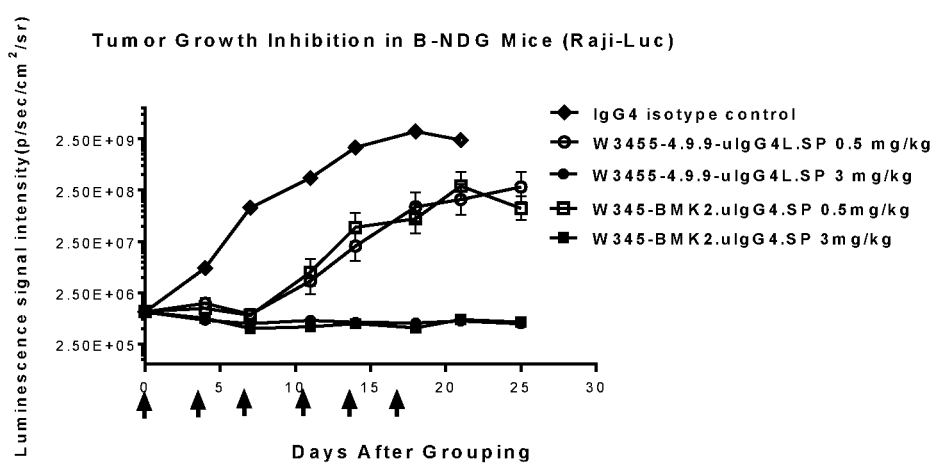
FIG. 14 shows the changes of luminescence signal intensity (corresponding to tumor growth) after treatment of lead antibody W3455 or benchmark antibodies at different concentrations.
Figure 15:
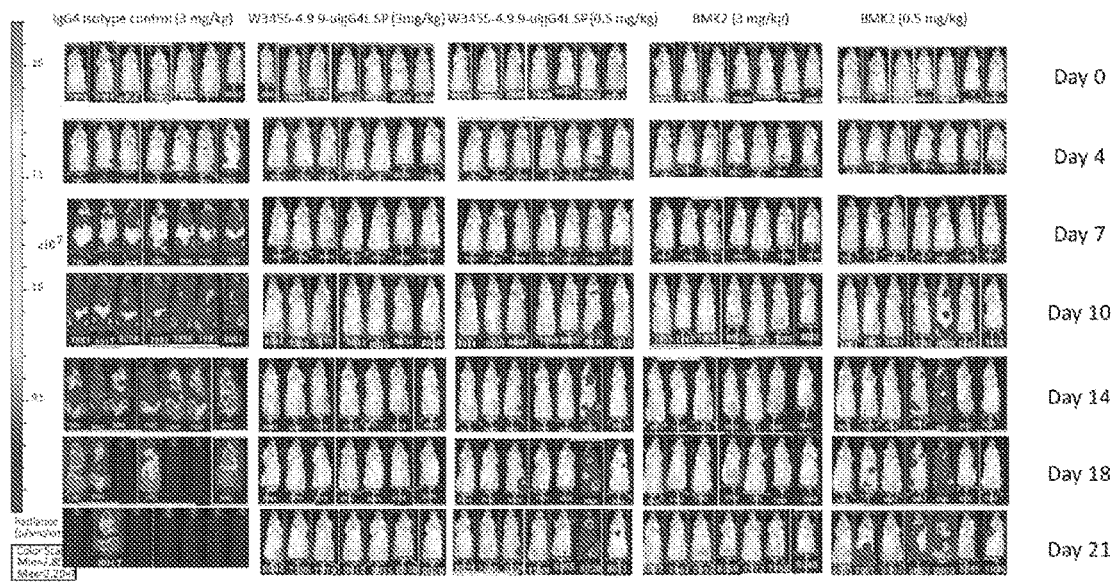
FIG. 15 shows live imaging photos of individual animal in B-NDG mice model post grouping. "BMK2" in this graph refers to W345-BMK2.uIgG4.SP (or abbreviated as "W345-BM K2").

As shown in FIG. 14, FIG. 15 and Table 12, at day 21 post grouping, compared with G1 (IgG4 isotype control, 3 mg/kg) vehicle group, the tumor growth inhibition (TGI %) of G2 group to G5 group were 100.0%, 93.2%, 100.0% and 87.5%, respectively. TGI (%)=[1−(Ti−T0)/(Vi−V0)]×100%, wherein Ti and Vi refer to the mean image signal value (i.e. luminescence signal intensity) in the treated and vehicle groups, respectively, on a given day. T0 and V0 refer to the mean image signal value in the treated and vehicle groups, respectively, on grouping day. In addition, the data showed statistical significant difference (P<0.05), which indicated the obvious anti-tumor efficacy of W3455-4.9.9-uIgG4L.SP and W345-BMK2.uIgG4.SP. The black arrow in FIG. 14 indicated the dosing time. Data was expressed as Mean±SEM, n=7.

Table 12. Tumor growth inhibition analysis

Tumor growth inhibition of at day 21 post grouping

| Dose (mg/kg) | Test articles | Tumor (p/sec/cm²/sr)[a] Before grouping | Day 21 post grouping | TGI (%) |
|---|---|---|---|---|
| 3 | Isotype IgG4 control | (1.05 ± 0.10) × 10⁶ | 2.39 × 10⁹ | — |
| 3 | WBP3455-4.9.9-uIgG4L.SP | (1.04 ± 0.11) × 10⁶ | (6.97 ± 4.73) × 10⁵ | 100.0 |
| 0.5 | WBP3455-4.9.9-uIgG4L.SP | (1.05 ± 0.10) × 10⁶ | (1.64 ± 1.60) × 10² | 93.2 |
| 3 | W345-BMK2.uIgG4.SP | (1.05 ± 0.07) × 10⁶ | (7.45 ± 0.77) × 10⁵ | 100.0 |
| 0.5 | W345-BMK2.uIgG4.SP | (1.07 ± 0.09) × 10⁶ | (3.01 ± 2.72) × 10⁸ | 87.5 |

Note:
[a] Mean ± SEM

Figure 16:
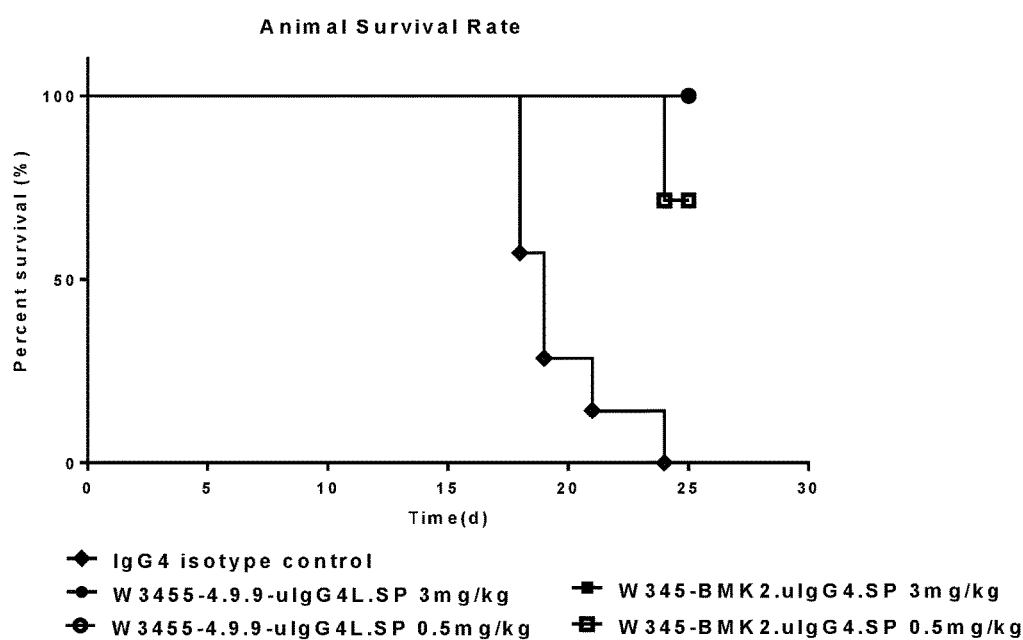
FIG. 16 shows animal survival rate in B-NDG mice model during days 0-32 post grouping.

Furthermore, the animal survival rate during days 0-25 post grouping was shown in FIG. 16. For the two WBP3455 groups at 3 and 0.5 mg/kg and the W345-BMK2 group at 3 mg/kg, no animal died. The result indicated that W3455-4.9.9-uIgG4L.SP showed better efficacy than W345-BMK2.uIgG4.SP and significantly prolonged the survival time of tumor-bearing mice.

In conclusion, the treatment of lead antibody W3455-4.9.9-uIgG4L.SP displayed significant anti-tumor efficacy, and showed as good as or slightly better result than W345-BMK2.uIgG4.SP. Furthermore, WBP3455-4.9.9-uIgG4L.SP significantly prolonged the survival time of tumor-bearing mice.

5.2 Anti-Tumor Efficacy in NCG Mice Model (HT-29 Cells)

Lead mAb efficacy study was tested on HT-29 colorectal adenocarcinoma model in NCG mice. Female NCG mice (Nanjing Galaxy Biopharmaceutical Co., LTD) of 7-8 weeks old were used in the study. The parental HT-29 cell line was purchased from ATCC. The cells were cultured in RPMI1640 medium supplemented with 10% heat inactivated fetal bovine serum at 37° C. in an atmosphere of 5% $CO_2$ in air. The tumor cells were routinely sub-cultured 2 to 3 times a week with 0.25% trypsin-EDTA treatment. The cells growing in an exponential growth phase were harvested and counted for tumor inoculation.

For the therapeutic model, the HT-29 cells (5.0×10⁶ cells/100 μL in PBS) were inoculated subcutaneously into NCG mouse. For all tumor studies, mice were weighed and tumor growth was measured twice a week using calipers. All the procedures related to animal handling, care and the treatment in the study were performed according to the guidelines approved by the Institutional Animal Care and Use Committee (IACUC) of Shanghai SIPPR-BK Laboratory Animal Co., Ltd following the guidance of the Association for Assessment and Accreditation of Laboratory Animal Care (AAALAC). Tumor volume was calculated with the formula ½ (length×width2). The results were represented by mean and the standard error (Mean±SEM). Data were analyzed using Two way RM ANOVA Tukey's multiple comparisons test with Graphpad Prism 6.0 and p<0.05 was considered to be statistically significant.

Figure 17:
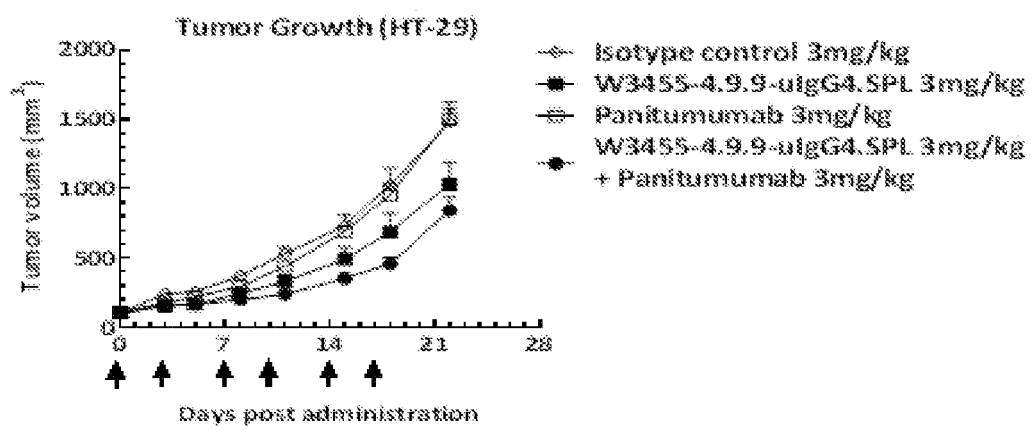
FIG. 17 shows the tumor volume changes in NCG mice inoculated with HT-29 cells after administration of lead antibody W3455 alone or in combination with panitumumab.

As shown in FIG. 17, the final lead antibody showed potent anti HT29 tumor cell efficacy in NCG mice, whose tumor cells are resistant to panitumumab. In addition, a synergic anti-tumor effect was observed in combo groups (WBP3455-4.9.9-uIgG4L.SP+panitumumab) with statistically significance (TGI~50%) on Day 15, Day17 and Day 22, as shown in FIG. 18.

5.3 Anti-Tumor Efficacy in CB-17 SCID Mice Model (Raji Cells)

Lead mAb anti-tumor efficacy study was tested on Raji B lymphatic cancer model in CB-17 SCID mice. Female CB-17 SCID mice (Shanghai Lingchang Biotech Co., LTD) of 7-8 weeks old were used in the study. The cells were cultured in RPMI1640 medium supplemented with 10% heat inactivated fetal bovine serum at 37° C. in an atmosphere of 5% $CO_2$ in air. The tumor cells were routinely sub-cultured 3 times a week. The cells growing in an exponential growth phase were harvested and counted for tumor inoculation.

For the therapeutic model, the Raji cells ($1.0 \times 10^6$ cells/200 μL in Matrigel/PBS mixture) were inoculated subcutaneously into CB-17 SCID mouse. Body weight was weighed and tumor growth was measured using calipers. When the tumor volume reached approximately 110 mm³, animals were randomly grouped into 5 groups, G1 (isotype control, 5 mg/kg) group, G2 (W345-BMK2, 1 mg/kg) group, G3 (W345-BMK8, 1 mg/kg) group, G4 (W3455-4.9.9-uIgG4L.SP, 5 mg/kg) group and G5 (W3455-4.9.9-uIgG4L.SP, 1 mg/kg) group, and the day of grouping was considered as day 0. Then they were injected intraperitoneally twice per week for a total of 6 times at day 0, day 4, day 7, day 11, day 14 and day 18 post grouping, respectively. For all tumor-bearing mice, body weight was weighed and tumor growth was measured twice a week using calipers. All the procedures related to animal handling, care and the treatment in the study were performed according to the guidelines approved by the Institutional Animal Care and Use Committee (IACUC) of Shanghai Model Organisms Animal Co., Ltd following the guidance of the Association for Assessment and Accreditation of Laboratory Animal Care (AAALAC).

Tumor volume was calculated with the formula ½ (length×width). The results were represented by mean and the standard error (Mean±SEM). Data were analyzed using Two way RM ANOVA Tukey's multiple comparisons test with Graphpad Prism and p<0.05 was considered to be statistically significant.

As shown in FIG. 19A and Table 13, at day 21 post grouping, mean body weight of the animals in G1 group to G5 group shown no significant reduction, which indicated W3455-4.9.9-uIgG4L.SP, W345-BMK2 and W345-BMK8 were not toxic.

As shown in FIG. 19B and Table 14, at day 21 post grouping, compared with the G1 (isotype control, 5 mg/kg) vehicle group, the tumor growth inhibition (TGI %) of G2 group to G5 group were 94.70%, 67.48%, 103.32% and 94.70%, respectively. In addition, the data showed statistically significant difference (P<0.05), which indicated the obvious anti-tumor efficacy of W3455-4.9.9-uIgG4L. SP, W345-BM K2 and W345-BMK8. Furthermore, W3455-4.9.9-uIgG4L. SP showed similar efficacy to W345-BMK2 at 1 mg/kg of dosing, and much better efficacy than W345-BMK8.

TABLE 13

Body weight before grouping and day 21 post grouping

| Groups | Test articles | Body weight (g)[a] before grouping | Body weight (g)[a] day 21 post grouping | P value [b] | Body weight change (g) |
|---|---|---|---|---|---|
| G1 | Isotype control 5 mg/kg | 17.89 ± 0.22 | 18.19 ± 0.61 | — | 0.30 |
| G2 | W345-BMK2 1 mg/kg | 18.21 ± 0.34 | 18.45 ± 0.40 | 0.729 | 0.24 |
| G3 | W345-BMK8 1 mg/kg | 17.98 ± 0.24 | 18.45 ± 0.41 | 0.725 | 0.47 |
| G4 | W3455-4.9.9-uIgG4L.SP 5 mg/kg | 18.21 ± 0.14 | 18.20 ± 0.39 | 0.983 | −0.01 |
| G5 | W3455-4.9.9-uIgG4L.SP 1 mg/kg | 18.21 ± 0.34 | 18.27 ± 0.30 | 0.907 | 0.06 |

Notes:
[a] Mean ± SEM.
[b] Statistical analysis of mean body weight at day 21 post grouping using T-test between G1 group and the treatment group.

TABLE 14

Tumor growth inhibition at day 21 post grouping

| Groups | Test articles | Tumor volume(mm³)[a] before grouping | Tumor volume (mm³)[a] day 21 post grouping | P value [b] | TGI (%) |
|---|---|---|---|---|---|
| G1 | Isotype control 5 mg/kg | 110.15 ± 3.40 | 1242.33 ± 222.22 | — | — |
| G2 | W345-BMK2 1 mg/kg | 110.20 ± 3.67 | 170.16 ± 45.90 | 0.000 | 94.70 |
| G3 | W345-BMK8 1 mg/kg | 110.29 ± 3.59 | 478.47 ± 84.49 | 0.007 | 67.48 |
| G4 | W3455-4.9.9-uIgG4L.SP 5 mg/kg | 110.72 ± 3.22 | 73.16 ± 13.42 | 0.000 | 103.32 |
| G5 | W3455-4.9.9-uIgG4L.SP 1 mg/kg | 110.04 ± 2.90 | 170.02 ± 61.56 | 0.001 | 94.70 |

Note:
[a] Mean ± SEM.
[b] Statistical analysis of mean body weight at day 21 post grouping using T-test between G1 group and the treatment group.

5.4 Pharmacokinetics and Toxicology Studies in Cynomolgus Monkeys

5.4.1 Pharmacokinetics Parameters

The lead mAb was evaluated for the pharmacokinetics (PK) in non-naïve cynomolgus monkeys. Four male monkeys (2 animal/group) were divided into 2 groups: low and high dose groups (15 and 50 mg/kg). Animals were intravenously administered with one single dose (see Table 15). The antibody was formulated in 20 mM Histidine, 5% sucrose solution at pH 5.0. The blood samples were collected at pre-dose (Day-1), 0.25 h, 0.5 h, 1 h, 4 h, 8 h, 24 h, Day 3, Day 7, Day 14, Day 21 and Day 28 for antibody concentration, which was determined by ELISA method and analyzed with WinNonlin software. Whole blood sample analyses for hematology (CBC) and serum chemistry were determined by hematology analyzer (ADVIA2120) and chemistry (HITACHI 7180), respectively. Cage-side observations for general health, appearance, and especially skin irritation were performed regularly.

TABLE 15

Grouping and testing antibody dosing information

| Test article | Number. of animals Male | Dose Level (mg/kg) | Dose Conc. (mg/mL) | Vehicle | Dosing Route |
|---|---|---|---|---|---|
| W3455-4.9.9-uIgG4.SPL | 2 | 15 | 13.2 | 20 mM Histidine, | IV bolus |
| W3455-4.9.9-uIgG4.SPL | 2 | 50 | 13.2 | 5% sucrose, pH 5.0 | |

TABLE 16

Pharmacokinetics parameters analysis

| mAb | W3455-4.9.9-uIgG4.SPL | |
|---|---|---|
| Dose | 15 mg/kg, IV, n = 2 | 50 mg/kg, IV, n = 2 |
| $t_{1/2}$ (h) | 48 | 86 |
| $C_{max}$ (µg/mL) | 366 | 852 |
| $AUC_{0-t}$ (µg/ml * h) | 10664 | 92672 |

Figure 20:
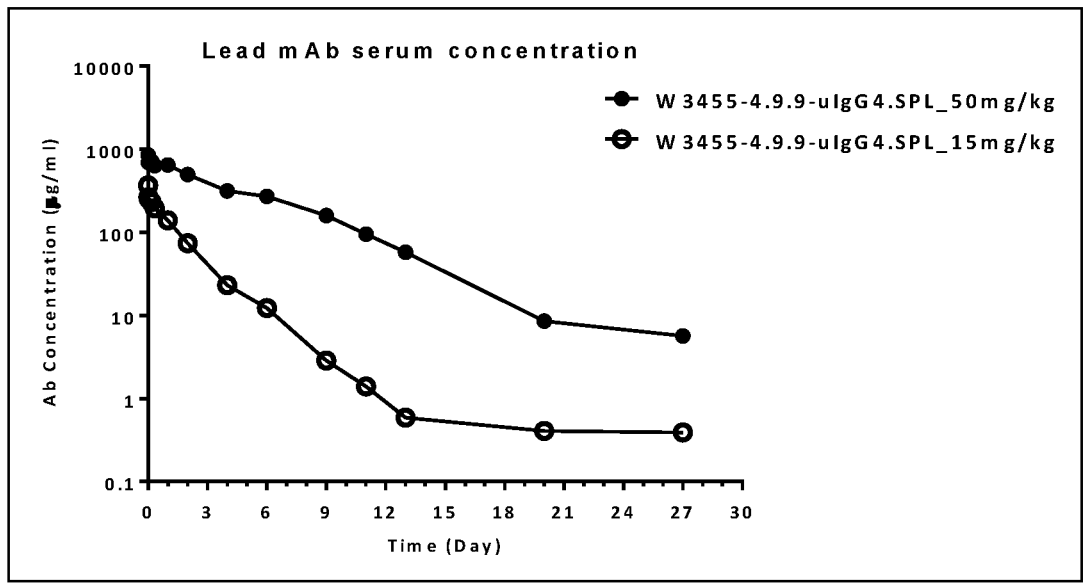
FIG. 20 shows the serum concentration of lead antibody W3455 in PK study in cynomolgus monkeys.

The average half-life ($T_{1/2}$) of W3455-4.9.9-uIgG4.SPL is 48 and 86 hours for 15 mg/kg and 50 mg/kg respectively, as shown in FIG. 20 and in Table 16. The data was expressed as mean value with n=2.

The systemic exposure for $C_{max}$ increased 2.3 fold for W3455-4.9.9-uIgG4.SPL as the dosage increased from 15 to 50 mg/kg, and $AUC_{0-t}$ increased 8.7 fold for W3455-4.9.9-uIgG4.SPL as the dosage increased from 15 to 50 mg/kg. In summary, the systemic exposure increased dose-proportionally as the dosage increased from 15 to 50 mg/kg.

5.4.2 Toxicology Study

Figure 21:
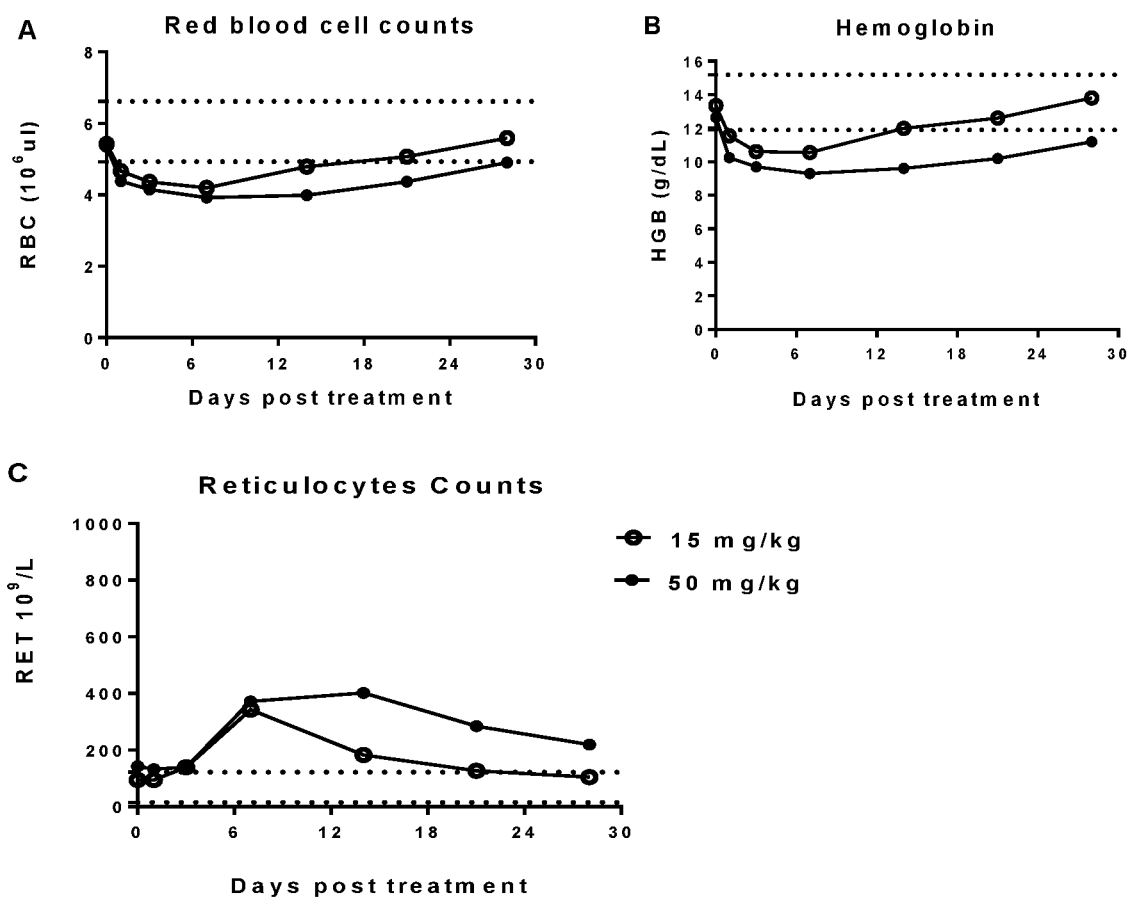
FIGS. 21A-21C show the changes of red blood cell counts (A), hemoglobin level (B), and reticulocyte counts (C) after administration of lead antibody W3455 in clinical hematology in cynomolgus monkeys.

The hematologic effect of lead mAb was evaluated in cynomolgus monkeys during the PK studies. The numbers of red blood cells (RBC) and reticulocytes were counted and the level of hemoglobin was quantified. The result was shown in FIG. 21, and data was expressed as mean value with n=2.

Administration of W3455-4.9.9-uIgG4.SPL caused a mild transient dose-dependent anemia. The nadir of RBCs count and hemoglobin (HGB) occurred about on day 7, and spontaneously returned to normal range in 1-2 weeks, as shown in FIG. 21A-B. The transient anemia was resolved with replacement by younger RBCs, since reticulocyte (RET) counts were significantly increased as early as day 3 and compensated the old aging RBC loss in blood (FIG. 21C).

Thus, we concluded that the anemia was transient and generally well-tolerated. The transient anemia was mild in the dose regimens administered and spontaneously recovered to the baseline levels after approximately two weeks. All 4 monkeys presented normal behaviors during the 28-day study period.

Those skilled in the art will further appreciate that the present disclosure may be embodied in other specific forms without departing from the spirit or central attributes thereof. In that the foregoing description of the present disclosure discloses only exemplary embodiments thereof, it is to be understood that other variations are contemplated as being within the scope of the present disclosure. Accordingly, the present invention is not limited to the particular embodiments that have been described in detail herein. Rather, reference should be made to the appended claims as indicative of the scope and content of the invention.

REFERENCES

[1] Michael H. Kershaw and Mark J. Smyth. Making macrophages eat cancer. Science 5 Jul. 2013 Vol 341.

[2] Chao M P, et al. Anti-CD47 antibody synergizes with rituximab to promote phagocytosis and eradicate non-Hodgkin lymphoma. Cell 2010; 142: 699-713.

[3] Brown E J, Frazier W A. Integrin-associated protein (CD47) and its ligands. Trends Cell Biol 2001; 11: 130-135

[4] Chao M P, et al. Therapeutic antibody targeting of CD47 eliminates human acute lymphoblastic leukemia. Cancer Res 2011; 71: 1374-1384.

[5] Liu J, et al. Pre-clinical development of a humanized anti-CD47 antibody with anti-cancer therapeutic potential. PloS One 2015; 10: e0137345. (BMK2)

[6] Patent: WO 2016/109415 A1; Jun. 17, 2016. (BMK1). CD47 Antibodies and Methods of use thereof.

[7] Patent: U.S. Pat. No. 9,017,675_B2; Humanized and chimeric monoclonal antibodies to CD47. (BMK2)

[8] Patent: US 2017/0081407 A1; Mar. 23, 2017. (BMK4). Anti-CD47 antibodies and methods of use.

[9] Patent: WO 2018/075857 A1; Apr. 26, 2018. (BMK8). Novel CD47 monoclonal antibodies and uses thereof

The invention claimed is:

1. An isolated antibody or antigen-binding portion thereof capable of binding that to CD47, wherein the isolated antibody or antigen-binding portion thereof comprises:
   a HCDR1 comprising the amino acid sequence of SEQ ID NO: 1;
   a HCDR2 comprising the amino acid sequence of SEQ ID NO: 2;
   a HCDR3 comprising the amino acid sequence of SEQ ID NO:3;
   a LCDR1 comprising the amino acid sequence of SEQ ID NO: 4;
   a LCDR2 comprising the amino acid sequence of SEQ ID NO: 5; and
   a LCDR3 comprising the amino acid sequence of SEQ ID NO: 6.

2. The isolated antibody or antigen-binding portion thereof of claim 1, wherein the isolated antibody or antigen binding portion thereof comprises:
   (A) a heavy chain variable region:
      (i) comprising the amino acid sequence of SEQ ID NO: 7; or
      (ii) comprising an amino acid sequence at least 85% identical to SEQ ID NO: 7; and
   (B) a light chain variable region:
      (iii) comprising the amino acid sequence of SEQ ID NO: 8; or
      (iv) comprising an amino acid sequence at least 85% identical to SEQ ID NO: 8.

3. The isolated antibody or antigen-binding portion thereof of claim 1, wherein the antibody further comprises a Fc region of a human IgG.

4. The isolated antibody or antigen-binding portion thereof of claim 3, wherein the Fc region is of human IgG4.

5. The isolated antibody or antigen-binding portion thereof of claim 4, wherein the Fc region of human IgG4 comprises a substitution of S228P, according to EU numbering.

6. The isolated antibody or antigen-binding portion thereof of claim 1, wherein the antibody is a chimeric antibody, a humanized antibody or a fully human antibody.

7. The isolated antibody or antigen-binding portion thereof of claim 1, wherein the isolated antibody or antigen-binding portion thereof comprises a heavy chain comprising SEQ ID NO: 11 and a light chain comprising SEQ ID NO: 12.

8. An isolated nucleic acid molecule, comprising a nucleic acid sequence encoding the isolated antibody or antigen binding portion thereof of claim 1.

9. A vector comprising the nucleic acid molecule of claim 8.

10. A host cell comprising the vector of claim 9.

11. A pharmaceutical composition comprising the antibody or antigen-binding portion thereof as defined in claim 1 and a pharmaceutically acceptable carrier.

12. A method for producing the antibody or antigen-binding portion thereof as defined in claim 1 comprising the steps of:
   culturing a host cell comprising a nucleic acid molecule(s) encoding the antibody or antigen-binding portion thereof under suitable conditions; and
   isolating the antibody or antigen-binding portion thereof from the host cell culture.

13. A method of inhibiting a CD47-related immune response in a subject, comprising administering to the subject the antibody or antigen-binding portion thereof as defined in claim 1.

14. A method for inhibiting growth of tumor cells and/or inducing macrophage-mediated phagocytosis of tumor cells in a subject, comprising administering an effective amount of the antibody or antigen-binding portion thereof as defined in claim 1 to the subject.

15. A method for treating cancer in a subject in need thereof, comprising administering an effective amount of the antibody or antigen-binding portion thereof as defined in claim 1 to the subject.

16. The method of claim 15, wherein the antibody or antigen-binding portion thereof is administered with a chemotherapeutic agent or a therapeutic antibody.

17. The method of claim 15, wherein the cancer is hematological cancer or a solid tumor.

18. The method of claim 17, wherein the hematological cancer is selected from acute lymphoblastic leukemia (ALL), acute myelogenous leukemia (AML), Non-Hodgkin lymphoma, Burkitt's lymphoma, B-lymphoblastic leukemia/lymphoma; B-cell chronic lymphocytic leukemia, chronic lymphocytic leukemia (CLL), chronic myelocytic leukemia (CML), follicular lymphoma, small lymphotic lymphoma (SLL), central nervous system (CNS) lymphoma, Richter's Syndrome, multiple myeloma, immunoblastic large cell lymphoma, precursor B-lymphoblastic lymphoma and anaplastic large cell lymphoma.

19. The method of claim 17, wherein the solid tumor is selected from lung cancer, pancreas cancer, breast cancer, liver cancer, ovary cancer, testicle cancer, kidney cancer, bladder cancer, brain cancer, cervix cancer, colon/rectum cancer, gastrointestinal tract cancer, skin cancer and prostate cancer.

20. A kit for treating or diagnosing cancers, comprising a container comprising at least one antibody or antigen-binding portion thereof as defined in claim 1.

\* \* \* \* \*